United States Patent
Hoekstra et al.

(10) Patent No.: US 8,754,227 B2
(45) Date of Patent: Jun. 17, 2014

(54) METALLOENZYME INHIBITOR COMPOUNDS

(75) Inventors: William J. Hoekstra, Durham, NC (US); Robert J. Schotzinger, Raleigh, NC (US); Stephen W. Rafferty, Durham, NC (US)

(73) Assignee: Viamet Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 13/561,586

(22) Filed: Jul. 30, 2012

(65) Prior Publication Data

US 2013/0005776 A1 Jan. 3, 2013

Related U.S. Application Data

(60) Division of application No. 13/093,530, filed on Apr. 25, 2011, now Pat. No. 8,236,962, which is a continuation of application No. PCT/US2011/033597, filed on Apr. 22, 2011.

(60) Provisional application No. 61/327,663, filed on Apr. 24, 2010.

(51) Int. Cl.
*A61K 31/44* (2006.01)
*C07D 401/00* (2006.01)

(52) U.S. Cl.
USPC ........................................ 546/268.1; 514/340

(58) Field of Classification Search
None
See application file for complete search history.

(56) References Cited

U.S. PATENT DOCUMENTS

| | | | |
|---|---|---|---|
| 4,616,026 A | 10/1986 | Richardson et al. | |
| 5,084,465 A | 1/1992 | Cuomo et al. | |

FOREIGN PATENT DOCUMENTS

| | | |
|---|---|---|
| JP | 2000-344744 A | 12/2000 |
| WO | 2004108684 A1 | 12/2004 |

OTHER PUBLICATIONS

Hiromichi Eto et al; New Antifungal 1,2,4-Triazoles with Difluoro(heteroaryl)methyl Moiety; Chem.Pharm.Bull, vol. 48, No. 7 (pp. 982-990), 2000.
Extended European Search Report for PCT/US2011/033597, 2013.

*Primary Examiner* — Heidi Reese
(74) *Attorney, Agent, or Firm* — Edwards Wildman Palmer LLP; Jeffrey D. Hsi; Stephen W. Rafferty

(57) ABSTRACT

The instant invention describes compounds having metalloenzyme modulating activity, and methods of treating diseases, disorders or symptoms thereof mediated by such metalloenzymes.

20 Claims, No Drawings

METALLOENZYME INHIBITOR COMPOUNDS

CROSS REFERENCE TO RELATED APPLICATIONS

This application is a divisional application of U.S. application Ser. No. 13/093,530, filed Apr. 25, 2011, which is a continuation application of PCT International Application No.: PCT/US11/33597, filed Apr. 22, 2011, which claims the benefit of U.S. Provisional Patent Application No. 61/327,663, filed Apr. 24, 2010, the contents of which are incorporated herein by reference in their entirety.

BACKGROUND

Living organisms have developed tightly regulated processes that specifically imports metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

A compound of formula (I), or salt, solvate, hydrate or prodrug thereof, wherein:

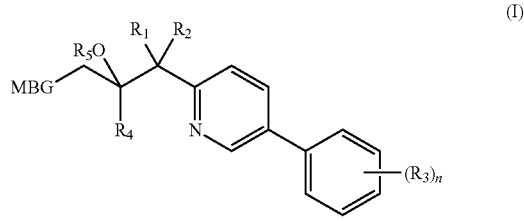

MBG is optionally substituted tetrazolyl, optionally substituted triazolyl, or optionally substituted pyrazolyl;
$R_1$ is halo;
$R_2$ is halo;
each $R_3$ is independently alkyl, cyano, haloalkyl, alkoxy, halo, haloalkoxy,
$R_4$ is aryl optionally substituted with 0, 1, 2 or 3 independent $R_3$;
$R_5$ is H, or —C(O)alkyl optionally substituted with amino;
n is 0, 1, 2 or 3.

Another aspect is a compound of the formulae herein, wherein the MBG is an optionally substituted 1H-tetrazol-1-yl, optionally substituted 2H-tetrazol-2-yl, optionally substituted 1H-1,2,4-triazol-1-yl, optionally substituted 1H-1,2,3-triazol-1-yl, or optionally substituted 1H-pyrazol-3-yl.

Another aspect is a compound of the formulae herein, wherein the MBG is unsubstituted 1H-tetrazol-1-yl, unsubstituted 2H-tetrazol-2-yl, unsubstituted 1H-1,2,4-triazol-1-yl, unsubstituted 1H-1,2,3-triazol-1-yl, or unsubstituted 1H-pyrazol-3-yl.

Another aspect is a compound of the formulae herein, wherein the MBG is 1H-tetrazol-1-yl.

Another aspect is a compound of the formulae herein, wherein $R_1$ is fluoro.

Another aspect is a compound of the formulae herein, wherein $R_2$ is fluoro.

Another aspect is a compound of the formulae herein, wherein $R_1$ and $R_2$ are fluoro.

Another aspect is a compound of the formulae herein, wherein $R_4$ is phenyl optionally substituted with 0, 1, 2 or 3 independent $R_3$.

Another aspect is a compound of the formulae herein, wherein $R_4$ is phenyl optionally substituted with 0, 1, 2 or 3 independent halo.

Another aspect is a compound of the formulae herein, wherein $R_4$ is phenyl optionally substituted with 0, 1, 2 or 3 independent fluoro.

Another aspect is a compound of the formulae herein, wherein R₄ is 2,4-difluorophenyl.

Another aspect is a compound of the formulae herein, wherein R₅ is H.

Another aspect is a compound of the formulae herein, wherein R₅ is amino substituted acyl.

Another aspect is a compound of the formulae herein, wherein:
R₁ is fluoro;
R₂ is fluoro;
R₄ is 2,4-difluorophenyl; and
R₅ is H.

Another aspect is a compound of the formulae herein, wherein:
each R₃ is independently cyano, haloalkyl, alkoxy, halo, haloalkoxy, and
n is 1 or 2, Another aspect is a compound of the formulae herein, wherein:
each R₃ is independently cyano, haloalkyl, alkoxy, halo, haloalkoxy, and
n is 1.

Another aspect is a compound of the formulae herein, wherein:
each R₃ is independently cyano, haloalkyl, alkoxy, halo, haloalkoxy, and
n is 1.

Another aspect is a compound of the formulae herein, wherein:
each R₃ is independently 4-cyano, 4-trifluoromethyl, 3-cyano, 4-isopropoxy, 4-fluoro, 3-trifluoromethoxy, 4-trifluoromethoxy, 3-chloro, 4-chloro, 2-fluoro, 5-fluoro, 4-(2,2,2-trifluoroethoxy), or 4-(3,3,3-trifluoro, 2,2-difluoropropoxy).

In one aspect, the compound of formula I is that wherein the compound inhibits (or is identified to inhibit) lanosterol demethylase (CYP51).

In one aspect, the compound of formula I is that wherein the compound is identified as having an activity range against a target enzyme and an activity range against an off-target enzyme (e.g., *C. albicans* MIC<0.02 μg/mL and IC50>16 μM for CYP2C9, CYP2C19 and CYP3A4; *C. albicans* MIC<0.10 μg/mL and IC50>10 μM for CYP2C9, CYP2C19 and CYP3A4; *C. albicans* MIC<0.5 μg/mL and IC50>15 μM for CYP2C9, CYP2C19 and CYP3A4).

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through a weaker interaction with the metal such as van der Waals interactions, pi cation interactions, pi-anion interactions, dipole-dipole interactions, ion-dipole interactions. In one aspect, the compound is identified as having a bonding interaction with the metal via the tetrazolyl moiety, triazolyl moiety, or pyrazolyl moiety, respectively. In one aspect, the compound is identified as having a bonding interaction with the metal via the 1-tetrazolyl moiety; in another aspect, the compound is identified as having a bonding interaction with the metal via the N2 of the 1-tetrazolyl moiety; in another aspect, the compound is identified as having a bonding interaction with the metal via the N3 of the 1-tetrazolyl moiety; in another aspect, the compound is identified as having a bonding interaction with the metal via the N4 of the 1-tetrazolyl moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In certain instances, the compounds of the invention are selected from the following of Formula (I) (and pharmaceutically acceptable salts, solvates, or hydrates thereof)

4-(6-(2-(2,4-Difluorophenyl)-1,1-difluoro-2-hydroxy-3-(1H-tetrazol-1-yl)propyl)pyridin-3-yl)benzonitrile (1);

2-(2,4-Difluorophenyl)-1,1-difluoro-3-(1H-tetrazol-1-yl)-1-(5-(4-(trifluoromethyl)phenyl)pyridin-2-yl)propan-2-ol (2);

3-(6-(2-(2,4-Difluorophenyl)-1,1-difluoro-2-hydroxy-3-(1H-tetrazol-1-yl)propyl)pyridin-3-yl)benzonitrile (3);

2-(2,4-Difluorophenyl)-1,1-difluoro-1-(5-(4-isopropoxyphenyl)pyridin-2-yl)-3-(1H-tetrazol-1-yl)propan-2-ol (4);

2-(2,4-Difluorophenyl)-1,1-difluoro-1-(5-(4-fluorophenyl)pyridin-2-yl)-3-(1H-tetrazol-1-yl)propan-2-ol (5);

2-(2,4-Difluorophenyl)-1,1-difluoro-3-(1H-tetrazol-1-yl)-1-(5-(3-(trifluoromethoxy)phenyl)pyridin-2-yl)propan-2-ol (6);

2-(2,4-Difluorophenyl)-1,1-difluoro-3-(H-tetrazol-1-yl)-1-(5-(4-(trifluoromethoxy)phenyl)pyridin-2-yl)propan-2-ol (7);

1-(5-(3-Chlorophenyl)pyridin-2-yl)-2-(2,4-difluorophenyl)-1,1-difluoro-3-(1H-tetrazol-1-yl)propan-2-ol (8);

1-(5-(4-Chlorophenyl)pyridin-2-yl)-2-(2,4-difluorophenyl)-1,1-difluoro-3-(1H-tetrazol-1-yl)propan-2-ol (9);

2-(2,4-Difluorophenyl)-1-(5-(2,5-difluorophenyl)pyridin-2-yl)-1,1-difluoro-3-(1H-tetrazol-1-yl)propan-2-ol (10);

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (11);

2-(2,4-Difluorophenyl)-1,1-difluoro-1-(5-(4-(2,2,3,3,3-pentafluoropropoxy)phenyl)phenyl)pyridin-2-yl)-3-(1H-tetrazol-1-yl)propan-2-ol (12);

2-(2,4-difluorophenyl)-1,1-difluoro-3-(1H-tetrazol-1-yl)-1-(5-(4-(2,2,2-trifluoroethoxy)phenyl)pyridin-2-yl)propan-2-yl 3-aminopropanoate (13);

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 2-aminoacetate hydrochloride (14).

2-(2,4-Difluorophenyl)-1,1-difluoro-3-(1H-pyrazol-3-yl)-1-(5-(4-(trifluoro methoxy)phenyl)pyridin-2-yl)propan-2-ol (15);

2-(2,4-Difluorophenyl)-1,1-difluoro-1-(5-(4-fluorophenyl)pyridin-2-yl)-3-(1H-1,2,4-triazol-1-yl)propan-2-ol (16);

2-(2,4-difluorophenyl)-1,1-difluoro-3-(1H-1,2,4-triazol-1-yl)-1-(5-(4-(2,2,2-trifluoroethoxy)phenyl)pyridin-2-yl)propan-2-ol (17);

2-(2,4-Difluorophenyl)-1,1-difluoro-3-(1H-1,2,4-triazol-1-yl)-1-(5-(4-(trifluoromethoxy)phenyl)pyridin-2-yl)propan-2-ol (18);

2-(2,4-Difluorophenyl)-1,1-difluoro-3-(1H-1,2,3-triazol-1-yl)-1-(5-(4-(trifluoromethoxy)phenyl)pyridin-2-yl)propan-2-ol (19);

2-(2,4-Difluorophenyl)-1,1-difluoro-3-(2H-tetrazol-1-yl)-1-(5-(4-(2,2,2-trifluoroethoxy)phenyl)pyridin-2-yl)propan-2-ol (20);

2-(2,4-Difluorophenyl)-1,1-difluoro-3-(2H-tetrazol-1-yl)-1-(5-(3-(fluorophenyl)pyridin-2-yl)propan-2-ol (21);

2-(2,4-Difluorophenyl)-1,1-difluoro-3-(2H-tetrazol-1-yl)-1-(5-(4-(trifluoromethylphenyl)pyridin-2-yl)propan-2-ol (22);

2-(2,4-Difluorophenyl)-1,1-difluoro-3-(1H-1,2,3-triazol-1-yl)-1-(5-(4-(trifluoromethylphenyl)pyridin-2-yl)propan-2-ol (23);

4-(6-(2-(2,4-Difluorophenyl)-1,1-difluoro-2-hydroxy-3-(1H-tetrazol-1-yl)propyl)pyridin-3-yl)phenol (24);

2-(2,4-Difluorophenyl)-1,1-difluoro-1-(5-(3-isopropylphenyl)pyridin-2-yl)-3-(1H-tetrazol-1-yl)propan-2-ol (25);

2-(2,4-Difluorophenyl)-1-(5-(3,4-difluorophenyl)pyridin-2-yl)-1,1-difluoro-3-(1H-tetrazol-1-yl)propan-2-ol (26);

1-(5-(3-(Difluoromethoxy)phenyl)pyridin-2-yl)-2-(2,4-Difluoropbenyl)-1,1-difluoro-3-(1H-tetrazol-1-yl)propan-2-ol (27);

2-(2,4-Difluorophenyl)-1,1-difluoro-3-(1H-tetrazol-1-yl)-1-(5-(4-((trifluoromethyl)thio)phenyl)pyridin-2-yl)propan-2-ol (28).

In another aspect, the invention provides a pharmaceutical composition comprising the compound of formula I and a pharmaceutically acceptable carrier.

In other aspects, the invention provides a method of modulating metalloenzyme activity in a subject, comprising contacting the subject with a compound of formula I, in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of formula I.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof an effective amount of a compound or pharmaceutical composition of formula I, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of formula I, such that metalloenzyme activity in said subject is modulated (e.g., down regulated, inhibited).

The methods herein include those wherein the disease or disorder is mediated by any of 4-hydroxyphenyl pyruvate dioxygenase, 5-lipoxygenase, adenosine deaminase, alcohol dehydrogenase, aminopeptidase n, angiotensin converting enzyme, aromatase (CYP19), calcineurin, carbamoyl phosphate synthetase, carbonic anhydrase family, catechol o-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase III, phosphodiesterase IV, phosphodiesterase V, pyruvate ferredoxin oxidoreductase, renal peptidase, ribonucleoside diphosphate reductase, thromboxane synthase (CYP5a), thyroid peroxidase, tyrosinase, urease, or xanthine oxidase.

The methods herein include those wherein the disease or disorder is mediated by any of 1-deoxy-d-xylulose-5-phosphate reductoisomerase (DXR), 17-alpha hydroxylase (CYP17), aldosterone synthase (CYP11B2), aminopeptidase p, anthrax lethal factor, arginase, beta-lactamase, cytochrome P450 2A6, d-ala d-ala ligase, dopamine beta-hydroxylase, endothelin converting enzyme-1, glutamate carboxypeptidase II, glutaminyl cyclase, glyoxalase, heme oxygenase, HPV/HSV E1 helicase, indoleamine 2,3-dioxygenase, leukotriene A4 hydrolase, methionine aminopeptidase 2, peptide deformylase, phosphodiesterase VII, relaxase, retinoic acid hydroxylase (CYP26), TNF-alpha converting enzyme (TACE), UDP-(3-O—(R-3-hydroxymyristoyl))-N-acetylglucosamine deacetylase (LpxC), vascular adhesion protein-1 (VAP-1), or vitamin D hydroxylase (CYP24).

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is prostate cancer, breast cancer, inflammatory bowel disease, psoriasis, systemic fungal infection, skin structure fungal infection, mucosal fungal infection, or onychomycosis.

The methods herein include those wherein the disease or disorder is cancer, cardiovascular disease, endocrinologic disease, inflammatory disease, infectious disease, gynecologic disease, metabolic disease, ophthalmologic disease, central nervous system (CNS) disease, urologic disease, gastrointestinal disease, superficial fungal infection, mucosal fungal infection, systemic fungal infection, or onychomycosis.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Another aspect of the invention is a composition comprising a compound of a formulae herein (e.g., formula (I)) and an agriculturally acceptable carrier.

Another aspect of the invention is a method of treating or preventing a metalloenzyme-mediated disease or disorder in or on a plant comprising contacting a compound herein with the plant.

Another aspect of the invention is a method of inhibiting metalloenzyme activity in or on a plant comprising contacting a compound herein with the plant.

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effective amount may range from about 1.0 pM to about 10 µM, from about 1.0 pM to about 50 µM, and from about 1.0 pM to about 100 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human. Veterinary uses or applications refer to use wherein the subject is an animal other than a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond, Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofilranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N''-ydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jihnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In one aspect, the invention provides a method of modulating the metalloenzyme activity of a cell in a subject, comprising contacting the subject with a compound of formula I, in an amount and under conditions sufficient to modulate metalloenzyme activity.

In one embodiment, the modulation is inhibition.

In another aspect, the invention provides a method of treating a subject suffering from or susceptible to a disorder or disease, comprising administering to the subject an effective amount of a compound or pharmaceutical composition of formula I such that said subject is treated for said disorder or the disorder is ameliorated.

In another aspect, the invention provides a method of treating a subject suffering from or susceptible to a metalloenzyme-mediated disorder or disease, comprising administering to the subject an effective amount of a compound or pharmaceutical composition of formula I.

In other aspects, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of formula I, such that said subject is treated for said disorder.

In certain embodiments, the invention provides a method of treating a disease, disorder or symptom thereof, wherein the disorder is cancer, cardiovascular disease, inflammatory disease or infectious disease. In other embodiments the disease, disorder or symptom thereof is metabolic disease, ophthalmologic disease, central nervous system (CNS) disease, urologic disease, or gastrointestinal disease. In certain embodiments the disease is prostate cancer, breast cancel; inflammatory bowel disease, psoriasis, systemic fungal infection, skin structure fungal infection, mucosal fungal infection, onychomycosis, or superficial fungal infection.

In another aspect, the compounds and compositions herein are useful for treating a disease, disorder or symptom thereof, which is associated with one or more of the following pathogenic fungi genera, including the genera and the species thereof herein: *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus filmigatus, Aspergillus niger, Blastomyces dermatitidis, Candida albicans, Candida glabrata, Candida guilliennondii, Candida krusei, Candida parapsilosis, Candida tropicalis, Candida pelliculosa, Cladophialophora carrionii, Coccidioides immitis, Cryptococcus neoformans, Cunninghamella sp., Epidermophyton floccosum, Exophiala dermatitidis, Filobasidiella neoformans, Fonsecaea pedrosoi, Fusarium solani, Geotrichum candidum, Histoplasma capsulatum, Hortaea werneckii,*

*Issatschenkia orientalis, Madurella grisae, Malassezia furfur, Malassezia globosa, Malassezia obtusa, Malassezia pachydermatis, Malassezia restricta, Malassezia slooffiae, Malassezia sympodialis, Microsporum canis, Microsporum filvum, Microsporum gypseum, Mucor circinelloides, Nectria haematococca, Paecilomyces variotii, Paracoccidioides brasiliensis, Penicillium marneffei, Pichia anomala, Pichia guilliermnnondii, Pneumocystis carinii, Pseudallescheria boydii, Rhizopus oryzae, Rhodotorula rubra, Scedosporium apiospernium, Schizophyllum commune, Sporothrix schenckii, Trichophyton mentagrophytes, Trichophyton rubrum, Trichophyton verrucosum, Trichophyton violaceum, Trichosporon asahii, Trichosporon cutaneum, Trichosporon inkin, Trichosporon mucoides.*

In another aspect, the compounds and compositions herein are useful for treating a disease, disorder or symptom thereof, which is associated with one of the following conditions: *Aspergillosis, Blastomycosis, Candidiasis, Chromomycosis, Coccidioidomycosis, Cryptococcosis, Demiatophytoses, Histoplasmosis, Keratomycosis, Lobomycosis, Malassezia infection, Mucormycosis, Paracoccidioidomycosis, Penicillium mameffei infection, Phaeohyphomycosis, Pneumocyctis pneumonia, Rhinosporidiosis, Sporotrichosis, Trichosporonosis, Zygomycosis.*

In another aspect, the compounds and compositions herein are useful for treating a disease, disorder or symptom thereof, which is Chagas disease (Genus *Trypanosoma*), African trypanosomiasis (Genus *Trypanosoma*), leishmaniasis (Genus *Leishmania*), tuberculosis (Genus *Mycobacterium*), leprosy (Genus *Mycobacterium*), malaria (Genus *Plasmodium*), tinea (capitis, corporis, pedis, tonsurans, versicolor).

In certain embodiments, the subject is a mammal, preferably a primate or human.

In another embodiment, the invention provides a method as described above, wherein the effective amount of the compound of formula I is as described above.

In another embodiment, the invention provides a method as described above, wherein the compound of formula I is administered intravenously, intramuscularly, subcutaneously, intracerebroventricularly, orally or topically.

In another embodiment, the invention provides a method as described herein wherein the compound of formula I demonstrates selectivity for an activity range against a target enzyme and an activity range against an off-target enzyme (e.g., *C. albicans* MIC<0.02 µg/mL and IC50>16 µM for CYP2C9, CYP2C19 and CYP3A4; *C. albicans* MIC<0.10 µg/mL and IC50>10 µM for CYP2C9, CYP2C19 and CYP3A4; *C. albicans* MIC<0.5 µg/mL and IC50>15 µM for CYP2C9, CYP2C19 and CYP3A4).

In other embodiments, the invention provides a method as described above, wherein the compound of formula I is administered alone or in combination with one or more other therapeutics. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, gastrointestinal disease agent, or anti-infective disease agent.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease.

Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Pharmaceutical Compositions

In one aspect, the invention provides a pharmaceutical composition comprising the compound of formula I and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of formula I, in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Agricultural Applications

The compounds and compositions herein can be used in methods of modulating metalloenzyme activity in a microorganism on a plant comprising contacting a compound herein with the plant (e.g., seed, seedling, grass, weed, grain).

The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen. As such, the compounds, compositions and agricultural uses herein include lawn, turf, ornamental vegetation, home and garden, farming, range and pasture applications. The microorganism can be any on a plant and include those delineated herein.

One aspect is a method of treating or preventing a fungal disease or disorder in or on a plant comprising contacting a compound of any of the formulae herein with the plant. Another aspect is a method of treating or preventing fungi growth in or on a plant comprising contacting a compound of any of the formulae herein with the plant. Another aspect is a method of inhibiting microorganisms in or on a plant comprising contacting a compound of any of the formulae herein with the plant.

The compositions comprising compounds herein can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds herein can be formulated as ordinary tablets, capsules, solids, liquids, emulsions, slurries, oils, fine granules or powders, which are suitable for administration to plants, fields or other agricultural areas. In preferred embodiments, the preparation includes between 1 and 95% (e.g., 1, 2, 3, 4, 5, 6, 7, 8, 9, 10, 25%, 75%, 80%, 90%, 95%) compound herein in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound herein is provided in an encapsulated formulation (liquid or powder). Specific materials suitable for use in capsule materials include, but are not limited to, porous particulates or substrates such as silica, perlite, talc, clay, pyrophillite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of active compound herein. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound herein is provided in an oil-based delivery system. Oil release substrates include vegetable and/or mineral oils. In one embodiment, the substrate also contains a surface active agent that renders the composition readily dispersable in water; such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound herein or combinations or derivatives thereof) useful in the prevention or treatment a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rape-seed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

The invention provides kits for the treatment or prevention of agricultural or plant disease or disorders. In one embodiment, the kit includes a composition containing an effective amount of a compound herein in a form suitable for delivery to a site plant. In some embodiments, the kit comprises a container which contains a compound of formula (I); such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder; precautions; warnings; description of research studies; and/or references. The instructions may be printed directly on the container (when present), or as a label applied to the container, or as a separate sheet, pamphlet, card, or folder supplied in or with the container.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of Antifungals

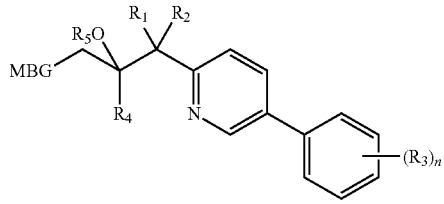
(I)

Syntheses of azole targets (1) may be accomplished using the example synthesis that is shown below (Scheme 1). A broad range of arenes and heterocycles, in addition to the 2-pyridine example below, may be prepared starting from functionalized halo-aromatic starting materials (e.g. 1). For the purpose of this example, R4 is a halogenated benzene moiety. An example synthesis of targets (I) commences with condensation of A with copper-activated ethyl α-bromo-difluoroacetate followed by condensation of the incipient ethyl ester product with lithiated bromodifluorobenzene to furnish ketone B (Scheme 1). The ketone is epoxidized with diazomethane to afford C. The bromo-pyridine intermediate C may be treated with aryl-boronic acids to introduce the R3-Ph moiety of D. The product D is obtained by then opening the epoxide with azole in the presence of a base such as potassium carbonate.

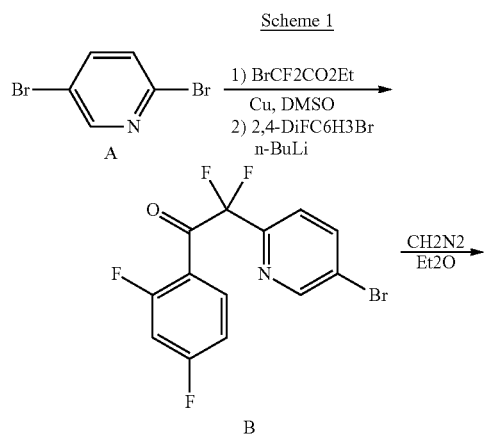

Scheme 1

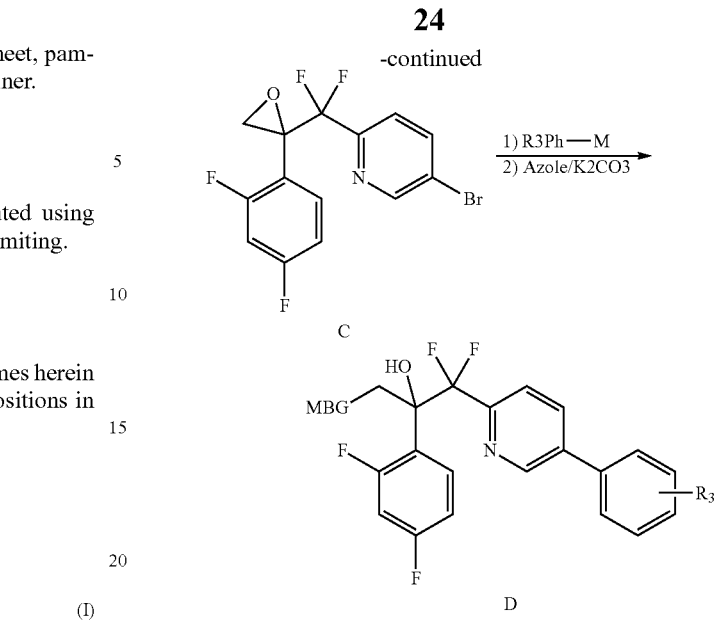

Synthesis of 2-(5-Bromopyridin-2-yl)-1-(2,4-difluorophenyl)-2,2-difluoroethanone (B)

To a suspension of copper powder (2.68 g, 42.2 mmol) in DMSO (35 mL) was added ethyl bromodifluoroacetate (2.70 mL, 21.10 mmol), and the mixture was stirred for 1 h at RT. 2,5-Dibromopyridine (2.50 g, 10.55 mmol) was then added and continued stirring for 15 h at RT. The reaction was quenched with aqueous $NH_4Cl$ and extracted with DCM (3×25 mL). The combined organic layers were washed with water, washed with brine, dried over anhydrous $Na_2SO_4$, and concentrated under reduced pressure to afford crude product mixture which upon column purification using EtOAc/hexane afforded the ethyl ester intermediate (2.40 g, 8.57 mmol, 81%) as a pale yellow oil. $^1H$ NMR (500 MHz, $CDCl_3$): δ 8.71 (s, 1H), 8.00 (d, J=9.0 Hz, 1H), 7.64 (d, J=9.0 Hz, 1H), 4.42-4.35 (m, 2H), 1.39-1.31 (m, 3H).

To a stirred solution of 2,4-difluoro-bromobenzene (1.65 g, 8.57 mmol) in diethyl ether (10 mL) was added n-BuLi (3.70 mL, 8.57 mmol) at −70° C. followed by addition of ester (2.40 g, 8.57 mmol) in diethyl ether (5 mL) after 15 minutes. The reaction mixture was stirred for 1 h at −70° C. and warmed to room temperature at which point another 2 h stirring was employed. The reaction was quenched with aqueous $NH_4CL$ solution and extracted with ethyl acetate (3×20 mL). The combined organic layers were washed with water, washed with brine, dried over anhydrous $Na_2SO_4$, and concentrated under reduced pressure. The crude compound was purified by column chromatography to afford ketone B (1.30 g, 3.73 mmol, 43%) as yellow liquid. $^1H$ NMR (500 MHz, $CDCl_3$): δ 8.62 (s, 1H), 8.08-8.04 (m, 2H), 7.74-7.70 (m, 1H), 7.05-6.95 (m, 1H), 6.88-6.78 (m, 1H). MS (ESI): 347, 349 [($M^+$+1)+2].

5-Bromo-2-((2-(2,4-difluorophenyl)oxiran-2-yl)difluoromethyl)pyridine (C)

To a stirred solution of ketone B (1.30 g, 3.73 mmol) in diethyl ether (300 mL) was added freshly prepared diazomethane at 0° C. followed by warming to RT. The reaction mixture was stirred for 2 h. The volatiles were removed under reduced pressure to afford a crude product mixture which upon column chromatography using EtOAc/hexane as the eluent afforded oxirane C (800 mg, 2.20 mmol, 59%) as light yellow solid. $^1H$ NMR (500 MHz, $CDCl_3$): δ 8.72 (s, 1H), 7.89 (d, J=9.0 Hz, 1H), 7.39-7.35 (m, 2H), 6.86-6.83 (m, 1H), 6.77-6.74 (m, 1H), 3.44 (s, 1H), 2.98 (s, 1H). MS (ESI): 362, 364 [($M^+$+1)+2].

Example 1

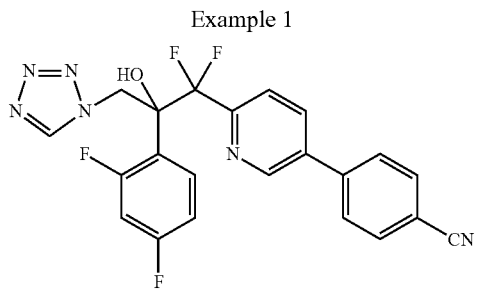

4-(6-(2-(2,4-Difluorophenyl)-1,1-difluoro-2-hydroxy-3-(1H-tetrazol-1-yl)propyl)pyridin-3-yl)benzonitrile (1)

To a stirred solution of epoxide C (0.3 g, 0.82 mmol) and 4-cyano-benzene boronic acid (0.14 g, 0.99 mmol) in 1,4-dioxane (5 mL) was added $K_2CO_3$ (0.17 g, 1.24 mmol) at RT under inert atmosphere. After purge with argon for a period of 30 min, Pd(dppf)$_2$Cl$_2$ (30 mg, 0.041 mmol) was added to the reaction mixture under argon atmosphere. The resulting mixture was stirred for 8 h at 75° C. Progress of the reaction was monitored by TLC. The solvent was evaporated under reduced pressure; the obtained residue was dissolved in water (20 mL). The aqueous layer was extracted with EtOAc (3×50 mL). The combined organic phases were washed with water, brine, dried over anhydrous $Na_2SO_4$ and concentrated. The crude material was purified by column chromatography to afford coupled product (0.15 g, 0.39 mmol, 47%) as a solid. $^1$H NMR (500 MHz, CDCl$_3$): δ 8.87 (s, 1H), 7.95 (dd, J=8.0, 2.0 Hz, 1H), 7.81-7.77 (m, 2H), 7.71-7.68 (m, 2H), 7.61 (d, J=8.0 Hz, 1H), 7.43 (app q, 1H), 6.87-6.83 (m, 1H), 6.77-6.73 (m, 1H), 3.48 (d, J=5.0 Hz, 1H), 3.00 (app s, 1H). MS (ESI): m/z 385 [M$^+$+1].

To a stirred solution of the coupled product (150 mg, 0.39 mmol) in DMF (3 mL) were added 1H-tetrazole (33 mg, 0.46 mmol) followed by $K_2CO_3$ (27 mg, 0.19 mmol) at RT under inert atmosphere. The reaction mixture was stirred for 16 h at 70° C. The reaction mixture was cooled to RT, diluted with water (5 mL) and extracted with ethyl acetate (2×20 mL). The organic layer was washed with water, brine and dried over anhydrous $Na_2SO_4$. After filtering off solid, the solvent was evaporated under reduced pressure to give crude compound. The crude compound was purified by column chromatography to afford compound 1 (50 mg, 0.11 mmol, 28%) as a white solid. $^1$H NMR (500 MHz, CDCl$_3$): δ 8.75 (s, 1H), 8.71 (s, 1H), 8.00 (dd, J=8.0, 2.0 Hz, 1H), 7.82 (d, J=7.0 Hz, 2H), 7.72 (d, J=8.5 Hz, 1H), 7.67 (d, J=7.0 Hz, 2H), 7.44-7.39 (m, 1H), 7.37 (s, 1H), 6.81-6.77 (m, 1H), 6.72-6.68 (m, 1H), 5.53 (d, J=14.5 Hz, 1H), 5.20 (d, J=14.5 Hz, 1H). HPLC: 99.6%. MS (ESI): m/z 455 [M$^+$+1].

Example 2

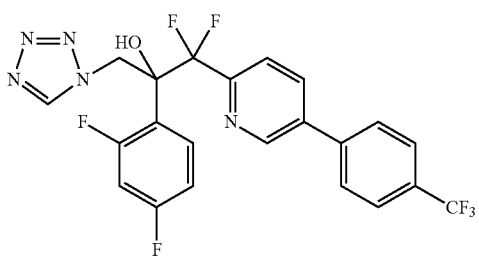 [SMILES: OC(Cn1cnnn1)(c1ccc(F)cc1F)C(F)(F)c1ccc(-c2ccc(C(F)(F)F)cc2)cn1]

2-(2,4-Difluorophenyl)-1,1-difluoro-3-(1H-tetrazol-1-yl)-1-(5-(4-(trifluoromethyl)phenyl)pyridin-2-yl)propan-2-ol (2)

To a stirred solution of bromo-epoxide C (0.25 g, 0.69 mmol) in THF (20 mL) and water (7 mL) were added 4-(trifluoromethyl)phenylboronic acid (0.10 g, 0.55 mmol), $Na_2CO_3$ (0.16 g, 1.55 mmol) and Pd(dppf)$_2$Cl$_2$ (0.14 g, 0.17 mmol) at RT under inert atmosphere. After purged with argon for a period of 30 min, the reaction mixture was heated to 75° C. and stirring was continued for 4 h. Progress of the reaction was monitored by TLC. The reaction mixture was cooled to RT and filtered through a pad of celite. The filtrate was concentrated under reduced pressure; obtained residue was dissolved in EtOAc (30 mL). The organic layer was washed with water, brine and dried over anhydrous $Na_2SO_4$ and concentrated under reduced pressure. The crude compound was purified by column chromatography to afford coupled product (0.21 g, 0.49 mmol, 71%) as solid. $^1$H NMR (500 MHz, CDCl$_3$): δ 8.90 (s, 1H), 7.95 (dd, J=8.5, 2.5 Hz, 1H), 7.77 (d, J=8.0 Hz, 2H), 7.71 (d, J=8.0 Hz, 2H), 7.60 (d, J=8.5 Hz, 1H), 7.45-7.40 (m, 1H), 6.85 (app t, 1H), 6.75 (app t, 1H), 3.48 (d, J=5.0 Hz, 1H), 3.00 (app s, 1H). Mass: m/z 428 [M$^+$+1].

To a stirred solution of coupled product (0.42 g, 0.98 mmol) in DMF (10 mL) was added $K_2CO_3$ (67 mg, 0.49 mmol) followed by 1H-tetrazole (68 mg, 0.98 mmol) at RT under inert atmosphere. The reaction mixture was stirred for 5 h at 80° C. The volatiles were removed under reduced pressure and obtained residue was dissolved in EtOAc (30 mL). The organic layer was washed with water, brine and dried over anhydrous $Na_2SO_4$ and concentrated under reduced pressure. The crude compound was purified by column chromatography to afford 2 (0.14 g, 0.28 mmol, 29%) as white solid. $^1$H NMR (500 MHz, CDCl$_3$): δ 8.76 (s, 1H), 8.73 (s, 1H), 8.01 (dd, J=8.0, 2.0 Hz, 1H), 7.78 (d, J=8.5 Hz, 2H), 7.72-7.67 (m, 3H), 7.49 (s, 1H), 7.44-7.37 (m, 1H), 6.81-6.76 (m, 1H), 6.71-6.65 (m, 1H), 5.57 (d, J=14.0 Hz, 1H), 5.19 (d, J=14.0 Hz, 1H). HPLC: 97.3%. Mass: m/z 498 [M$^+$+1].

Chiral Preparative HPLC of Enantiomers:

The enantiomers of 2 (150 mg, 0.3 mmol) were separated by normal-phase preparative high performance liquid chromatography (Chiralpak IC, 250×21.2 mm, 5µ; using (A) n-hexane-(B) IPA (A:B: 60:40) as a mobile phase; flow rate: 11 mL/min) to obtain 2(+) (40 mg) and 2(−) (40 mg).

Analytical data for 2 (+):

HPLC: 100%.

Chiral HPLC: $R_t$=22.7 min (Chiralpak IC, 250×4.6 mm, 5µ; mobile phase (A) n-Hexane (B) IPA (6/4): A:B (60:40); flow Rate: 1.00 mL/min)

Optical rotation $[α]_D^{25}$: +18° (C=0.1% in MeOH).

Example 3

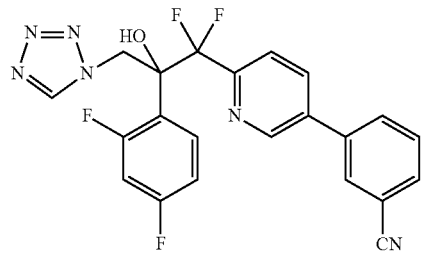 [SMILES: N#Cc1cccc(-c2ccc(C(F)(F)C(O)(Cn3cnnn3)c3ccc(F)cc3F)nc2)c1]

3-(6-(2-(2,4-Difluorophenyl)-1,1-difluoro-2-1hydroxy-3-(1H-tetrazol-1-yl)propyl)pyridin-3-yl)benzonitrile (3)

Compound 3 was prepared using the conditions employed for 1. 0.020 g as a tan solid. 1H NMR (500 MHz, CDCl$_3$): δ

8.76 (s, 1H), 8.71 (s, 1H), 7.99 (dd, J=8.0, 2.0 Hz, 1H), 7.84 (s, 1H), 7.80-7.76 (m, 2H), 7.72 (d, J=8.0 Hz, 1H), 7.65 (t, J=7.5 Hz, 1H), 7.43-7.38 (m, 2H), 6.81-6.76 (m, 1H), 6.72-6.68 (m, 1H), 5.54 (d, J=14.5 Hz, 1H), 5.20 (d, J=14.5 Hz, 1H). HPLC: 93.95%. MS (ESI): m/z 455 [M$^+$+1].

Example 4

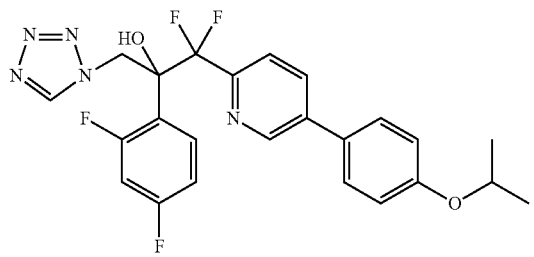 [SMILES: CC(C)Oc1ccc(-c2ccc(C(F)(F)C(O)(Cn3cnnn3)c3ccc(F)cc3F)nc2)cc1]

2-(2,4-Difluorophenyl)-1,1-difluoro-1-(5-(4-isopropoxyphenyl)pyridin-2-yl)-3-(1H-tetrazol-1-yl)propan-2-ol (4)

Compound 4 was prepared using the conditions employed for 1: 0.029 g as a white solid. $^1$H NMR (500 MHz, CDCl$_3$): δ 8.76 (s, 1H), 8.71 (s, 1H), 7.94 (dd, J=8.5, 2.5 Hz, 1H), 7.82 (s, 1H), 7.61 (d, J=8.0 Hz, 1H), 7.50-7.47 (m, 2H), 7.40-7.35 (m, 1H), 7.01-6.98 (m, 2H), 6.79-6.74 (m, 1H), 6.68-6.64 (m, 1H), 5.61 (d, J=14.0 Hz, 1H), 5.10 (d, J=14.0 Hz, 1H), 4.64-4.59 (m, 1H), 1.37 (d, J=6.0 Hz, 6H). HPLC: 99.1%. MS (ESI): m/z 488 [M$^+$+1].

Example 5

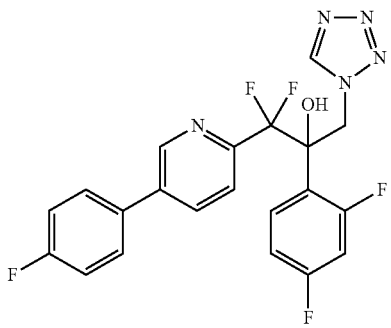 [SMILES: OC(Cn1cnnn1)(c1ccc(F)cc1F)C(F)(F)c1ccc(-c2ccc(F)cc2)cn1]

2-(2,4-Difluorophenyl)-1,1-difluoro-1-(5-(4-fluorophenyl)pyridin-2-yl)-3-(1H-tetrazol-1-yl)propan-2-ol (5)

Compound 5 was prepared using the conditions employed for 1: 0.033 g as a white solid. $^1$H NMR (500 MHz, CDCl$_3$): δ 8.76 (s, 1H), 8.69 (s, 1H), 7.95 (dd, J=8.0, 2.0 Hz, 1H), 7.66 (d, J=8.5 Hz, 2H), 7.55-7.52 (m, 2H), 7.42-7.37 (m, 1H), 7.22-7.19 (m, 2H), 6.80-6.75 (m, 1H), 6.70-6.66 (m, 1H), 5.58 (d, J=14.5 Hz, 1H), 5.15 (d, J=14.5 Hz, 1H). HPLC: 99.7%. MS (ESI): m/z 448 [M$^+$+1].

Example 6

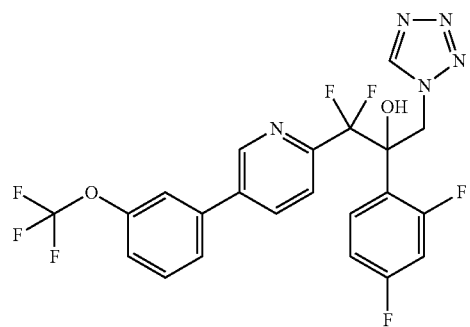 [SMILES: OC(Cn1cnnn1)(c1ccc(F)cc1F)C(F)(F)c1ccc(-c2cccc(OC(F)(F)F)c2)cn1]

2-(2,4-Difluorophenyl)-1,1-difluoro-3-(1H-tetrazol-1-yl)-1-(5-(3-(trifluoromethoxy)phenyl)pyridin-2-yl)propan-2-ol (6)

Compound 6 was prepared using the conditions employed for 1: 0.028 g as a yellow solid. $^1$H NMR (500 MHz, CDCl$_3$): δ 8.76 (s, 1H), 8.73 (s, 1H), 7.98 (dd, J=8.0, 2.2 Hz, 1H), 7.69 (d, J=8.5 Hz, 1H), 7.57-7.49 (m, 3H), 7.41-7.33 (m, 3H), 6.80-6.75 (m, 1H), 6.70-6.66 (m, 11H), 5.59 (d, J=14.5 Hz, 1H), 5.16 (d, J=14.5 Hz, 1H). HPLC: 97.2%. MS (ESI): m/z 514 [M$^+$+1].

Example 7

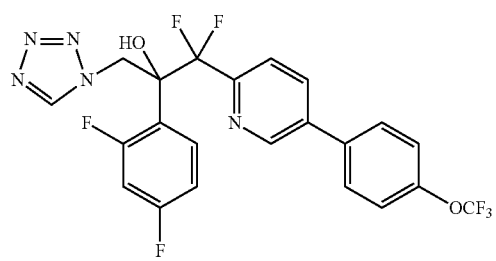 [SMILES: OC(Cn1cnnn1)(c1ccc(F)cc1F)C(F)(F)c1ccc(-c2ccc(OC(F)(F)F)cc2)cn1]

2-(2,4-Difluorophenyl)-1,1-difluoro-3-(1H-tetrazol-1-yl)-1-(5-(4-(trifluoromethoxy)phenyl)pyridin-2-yl)propan-2-ol (7)

To a stirred solution of bromo epoxide C (0.5 g, 1.38 mmol) in THF (30 mL) and water (14 mL) were added 4-(trifluoromethoxy)phenylboronic acid (0.22 g, 1.1 mmol), Na$_2$CO$_3$ (0.32 g, 3.1 mmol) and Pd(dppf)$_2$Cl$_2$ (0.28 g, 0.34 mmol) at RT under inert atmosphere. After purged with argon for a period of 30 min, the reaction mixture was heated to 75° C. and stirring was continued for 4 h. Progress of the reaction was monitored by TLC. The reaction mixture was cooled to RT and filtered through a pad of celite. The filtrate was concentrated under reduced pressure; obtained residue was dissolved in ethyl acetate (30 mL). The organic layer was washed with water, brine and dried over anhydrous Na$_2$SO$_4$ and concentrated under reduced pressure. The crude compound was purified by column chromatography to afford the coupled product (0.45 g, 1.0 mmol, 73%) as solid. ¹H NMR (200 MHz, CDCl₃): δ 8.87 (s, 1H), 7.90 (dd, J=8.2, 2.2 Hz, 1H), 7.66-7.54 (m, 3H), 7.49-7.34 (m, 3H), 6.90-6.70 (m, 2H), 3.49 (d, J=5.0 Hz, 1H), 3.02-2.95 (m, 1H). Mass: m/z 444 [M⁺+1].

To a stirred solution of the coupled product (0.45 g, 1.0 mmol) in DMF (10 mL) was added $K_2CO_3$ (70 mg, 0.5 mmol) followed by 1H-tetrazole (70 mg, 1.0 mmol) at RT under inert atmosphere. The reaction mixture was stirred for 4 h at 80° C. The volatiles were removed under reduced pressure and obtained residue was dissolved in water (15 mL) and extracted with ethyl acetate (2×20 mL). The combined organic layers were washed with water, brine and dried over anhydrous $Na_2SO_4$ and concentrated under reduced pressure. The crude compound was purified by column chromatography to afford 7 (0.19 g, 0.37 mmol, 36%) as white solid. ¹H NMR (500 MHz, CDCl₃): δ 8.76 (s, 1H), 8.70 (s, 1H), 7.97 (dd, J=8.0, 2.0 Hz, 1H), 7.68 (d, J=8.5 Hz, 1H), 7.60-7.56 (m, 3H), 7.43-7.36 (m, 3H), 6.80-6.76 (m, 1H), 6.70-6.67 (m, 1H), 5.57 (d, J=14.5 Hz, 1H), 5.17 (d, J=14.5 Hz, 1H). HPLC: 98.3%. Mass: m/z 513.9 [M⁺+1].

Chiral Preparative HPLC of Enantiomers:

The enantiomers of 7 (17.8 g, 34.6 mmol) were separated by normal-phase preparative high performance liquid chromatography (Chiralpak AD-H, 250×21.2 mm, 5μ; using (A) n-hexane-(B) IPA (A:B: 70:30) as a mobile phase; Flow rate: 15 mL/min) to obtain 7(+) (6.0 g) and 7(−) (5.8 g).

Analytical data for 7 (+):

HPLC: 99.8%.

Chiral HPLC: $R_t$=9.88 min (Chiralpak AD-H, 250×4.6 mm, 5μ; mobile phase (A) n-Hexane (B) IPA (7/3): A:B (70:30); flow Rate: 1.00 mL/min)

Optical rotation $[α]_D^{25}$: +19° (C=0.1% in MeOH).

Example 8

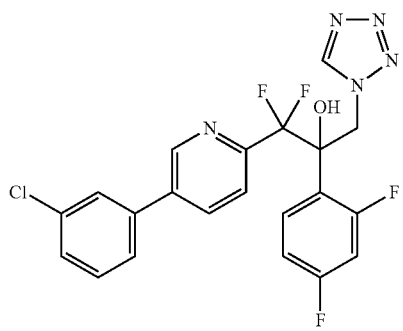 [SMILES: OC(Cn1cnnn1)(c1ccc(F)cc1F)C(F)(F)c1ccc(-c2cccc(Cl)c2)cn1]

1-(5-(3-Chlorophenyl)pyridin-2-yl)-2-(2,4-difluorophenyl)-1,1-difluoro-3-(1H-tetrazol-1-yl)propan-2-ol (8)

Compound 37 was prepared using the conditions employed for 1: 0.028 g as a white solid. ¹H NMR (500 MHz, CDCl₃): δ 8.76 (s, 1H), 8.72 (s, 1H), 7.97 (dd, J=8.5, 2.2 Hz, 1H), 7.67 (d, J=8.0 Hz, 1H), 7.56-7.54 (m, 2H), 7.46-7.43 (m, 3H), 7.40-7.35 (m, 1H), 6.80-6.75 (m, 1H), 6.70-6.66 (m, 1H), 5.59 (d, J=14.5 Hz, 1H), 5.16 (d, J=14.5 Hz, 1H). HPLC: 98.79%. MS (ESI): m/z 463.9 [M⁺].

Example 9

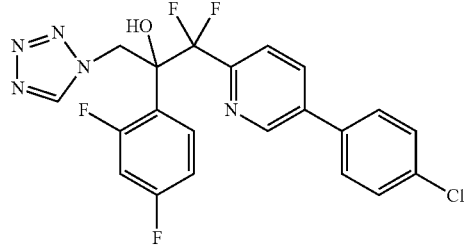 [SMILES: OC(Cn1cnnn1)(c1ccc(F)cc1F)C(F)(F)c1ccc(-c2ccc(Cl)cc2)cn1]

1-(5-(4-Chlorophenyl)pyridin-2-yl)-2-(2,4-difluorophenyl)-1,1-difluoro-3-(1H-tetrazol-1-yl)propan-2-ol (9)

Compound 9 was prepared using the conditions employed for 1: 0.027 g as a white solid. ¹H NMR (500 MHz, CDCl₃): δ 8.75 (s, 1H), 8.70 (s, 1H), 7.96 (d, J=8.5 Hz, 1H), 7.66 (d, J=8.5 Hz, 1H), 7.60 (s, 1H), 7.49 (s, 4H), 7.42-7.37 (m, 1H), 6.79-6.76 (m, 1H), 6.70-6.67 (m, 1H), 5.58 (d, J=14.5 Hz, 1H), 5.16 (d, J=14.5 Hz, 1H). HPLC: 99.07%. MS (ESI): m/z 463.9 [M⁺].

Chiral Preparative HPLC of Enantiomers:

The enantiomers of 9 (200 mg, 0.4 mmol) were separated by normal-phase preparative high performance liquid chromatography (Chiralpak IC, 250×21.1 mm, 5μ; using (A) n-hexane-(B) ethanol (A:B: 75:25) as a mobile phase; Flow rate: 15 mL/min) to obtain 9(+) (62 mg) and 9(−) (55 mg).

Analytical Data for 9 (+):

HPLC: 100%

Chiral HPLC: $R_t$=15.3 min (Chiralpak IC, 250×4.6 mm, 5μ; mobile phase (A) n-Hexane (B) ethanol: A:B (75:25); flow Rate: 1.00 mL/min)

Optical rotation $[α]_D^{25}$: +26.50 (C=0.1% in MeOH).

Example 10

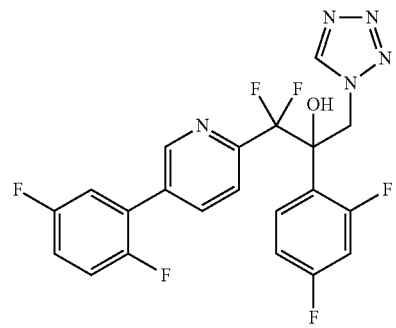 [SMILES: OC(Cn1cnnn1)(c1ccc(F)cc1F)C(F)(F)c1ccc(-c2cc(F)ccc2F)cn1]

2-(2,4-Difluorophenyl)-1-(5-(2,5-difluorophenyl)pyridin-2-yl)-1,1-difluoro-3-(1H-tetrazol-1-yl)propan-2-ol (10)

Compound 10 was prepared using the conditions employed for 1: 0.022 g as a yellow solid. ¹H NMR (500 MHz, CDCl₃): δ 8.76 (s, 1H), 8.70 (s, 1H), 7.98 (d, J=8.0 Hz, 1H), 7.69 (d, J=8.0 Hz, 1H), 7.49 (s, 1H), 7.41-7.36 (m, 1H), 7.20-7.11 (m, 3H), 6.79-6.75 (m, 1H), 6.70-6.67 (m, 1H), 5.60 (d, J=14.5 Hz, 1H), 5.16 (d, J=14.5 Hz, 1H). HPLC: 98.68%. MS (ESI): m/z 466 [M⁺].

Example 11

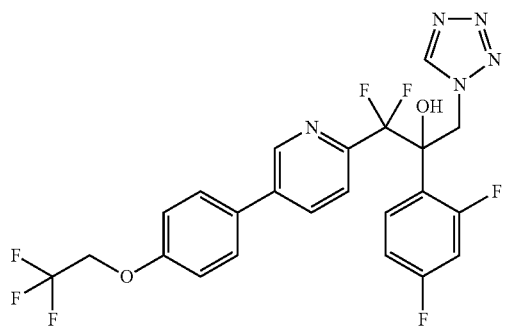 [SMILES: OC(Cn1cnnn1)(c1ccc(F)cc1F)C(F)(F)c1ccc(-c2ccc(OCC(F)(F)F)cc2)cn1]

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (11)

Compound 11 was prepared using the conditions employed for 1: 0.33 g as a solid. The precursor 1-bromo-4-(2,2,2-trifluoroethoxy)benzene was prepared as described below in one step.

$^1$H NMR (500 MHz, CDCl$_3$): δ 8.76 (s, 1H), 8.70 (s, 1H), 7.95 (d, J=8.0 Hz, 1H), 7.70 (s, 1H), 7.64 (d, J=8.5 Hz, 1H), 7.54 (d, J=8.5 Hz, 2H), 7.42-7.37 (m, 1H), 7.08 (d, J=8.5 Hz, 2H), 6.79-6.75 (m, 1H), 6.69-6.66 (m, 1H), 5.58 (d, J=14.0 Hz, 1H), 5.14 (d, J=14.0 Hz, 1H), 4.44-4.39 (m, 2H). HPLC: 99.1%. MS (ESI): m/z 528 [M$^+$+1].

Chiral Preparative HPLC SPECIFICATIONS for (+)-11:
Column: Chiralpak IA, 250×4.6 mm, 5µ
Mobile Phase: A) n-Hexane, B) IPA
Isocratic: A:B (65:35)
Flow Rte: 1.00 mL/min
Optical rotation [α]$_D$: +24° (C=0.1% in MeOH).

1-Bromo-4-(2,2,2-trifluoroethoxy)benzene

To a stirred solution of trifluoroethyl tosylate (1.5 g, 5.8 mmol) in DMF (20 mL) was added K$_2$CO$_3$ (4 g, 29.4 mmol) followed by addition of p-bromo phenol (1.1 g, 6.46 mmol) at RT under inert atmosphere. The reaction mixture was stirred at 120° C. for 6 h. The volatiles were evaporated under reduced pressure; the residue was diluted with water (5 mL) and extracted with ethyl acetate (3×30 mL). The organic layer was washed with water, brine and dried over anhydrous Na$_2$SO$_4$, filtered and concentrated in vacuo. The crude compound was purified by silica gel column chromatography eluting with 5% EtOAc/hexane to afford the desired product (0.8 g, 3.13 mmol, 53.3%) as semi solid. $^1$H NMR (200 MHz, CDCl$_3$): δ 7.44-7.38 (m, 2H), 6.86-6.80 (m, 2H), 4.38-4.25 (m, 2H).

Example 12

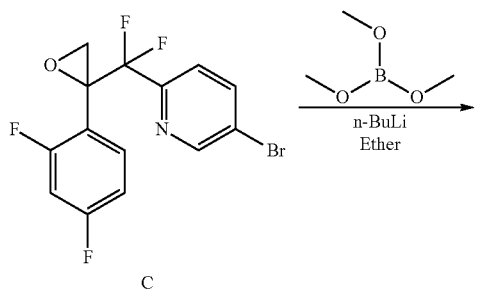

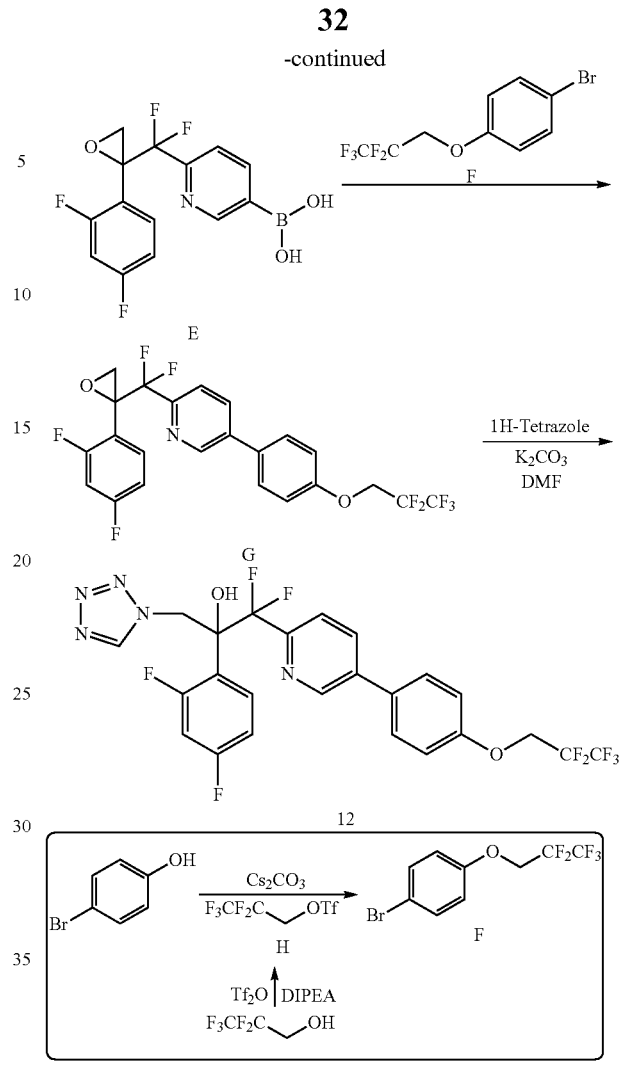

2-(2,4-Difluorophenyl)-1,1-difluoro-1-(5-(4-(2,2,3,3,3-pentafluoropropoxy)phenyl)pyridin-2-yl)-3-(1H-tetrazol-1-yl)propan-2-ol (12)

To a stirred solution of trifluoroethanol (10 g, 0.06 mol) in dry CH$_2$Cl$_2$ (100 mL) was added DIPEA (29 mL, 0.16 mol) at RT and the reaction mixture was cooled to −78° C. Triflic anhydride (13.5 mL, 0.07 mol) was added dropwise to the reaction mixture at −78° C. After being stirred for 30 min, the reaction mixture was warmed to −30° C. and stirring was continued for another 30 min. The reaction mixture was quenched with water (200 mL) and extracted with CH$_2$Cl$_2$ (2×300 mL). The combined organic layers were washed with 1 N HCl, water, dried over anhydrous Na$_2$SO$_4$ and filtered. To a stirred solution of 4-bromophenol (4 g, 0.02 mol), Cs$_2$CO$_3$ (15 g, 0.04 mol) in DMF (100 mL) was added CH$_2$Cl$_2$ layer (H) at RT and stirred for 16 h. The progress of the reaction was monitored by TLC. The reaction mixture was diluted with water and extracted with CH$_2$Cl$_2$ (2×250 mL). The combined organic layers were dried over anhydrous Na$_2$SO$_4$, filtered and concentrated under reduced pressure. The obtained crude material was purified by column chromatography (SiO$_2$, 60-120 mesh) to afford compound F (3.5 g, 11.5 mmol, 50%) as a liquid. $^1$H NMR (200 MHz, CDCl$_3$): δ 7.46-7.38 (m, 2H), 6.87-6.79 (m, 2H), 4.45-4.32 (m, 2H).

To a stirred solution of n-BuLi (21 mL, 33.13 mmol, 1.5 M in hexane) in dry ether (250 mL) was added a solution of compound C (8 g, 22.09 mmol) in ether (50 mL) at −78° C. After being stirred for 30 min, trimethyl borate (5 mL, 44.19 mmol) was added to the reaction mixture at −78° C. and the stirring was continued for another 10 min. The reaction mixture was allowed to warm to room temperature and stirred for 30 min. The reaction mixture was quenched with acetic acid (40 mL) and diluted with water (120 mL) and stirred for 1 h at RT. The reaction mixture was basified to 2N pH~12 by addition of 2N NaOH, the organic layer was separated and the aqueous layer was acidified to pH~6 using 1N HCl. The aqueous layer was extracted with $CH_2Cl_2$ (2×500 mL). The combined organic layers were dried over anhydrous $Na_2SO_4$ and concentrated under reduced pressure to afford compound E (7 g, 21.4 mmol, 97%) as a brown white solid. $^1$H NMR (500 MHz, $CD_3OD$): δ 8.81 (s, 1H), 8.15 (d, J=7.5 Hz, 1H), 7.47 (d, J=8 Hz, 1H), 7.36-7.35 (m, 1H), 6.93-6.87 (m, 2H), 3.42 (d, J=5.5 Hz, 1H), 2.99-2.98 (m, 1H). MS (ESI): m/z 328.1 [M$^+$+1]. A mixture of boronic acid E (3.5 g, 10.7 mmol), compound F (3.3 g, 10.7 mol) and $K_2CO_3$ (4.5 g, 32.1 mmol) in THF/$H_2O$ (175 mL, 4:1) was degassed for 30 min. Pd (dppf)$_2$Cl$_2$ (0.7 g, 1.07 mmol) was added to the reaction mixture under an inert atmosphere and the resulting mixture was stirred at 70° C. for 2 h. The reaction mixture was allowed to cool to room temperature and the volatiles were removed under reduced pressure. The obtained crude material was purified by column chromatography (SiO$_2$, 60-120 mesh) to afford compound G (2.3 g, 4.53 mmol, 43%) as off-white solid. $^1$H NMR (200 MHz, CDCl$_3$): δ 8.83 (d, J=2.2 Hz, 1H), 7.90 (dd, J=2.2, 8.0 Hz, 1H), 7.61-7.48 (m, 3H), 7.43-7.36 (m, 1H), 7.29 (d, J=8.8 Hz, 2H), 7.10-7.04 (m, 2H), 6.89-6.70 (m, 2H), 4.48 (q, J=12.4 Hz, 2H), 3.45 (d, J=5.0 Hz, 1H), 3.01-2.98 (m, 1H).

To a stirred solution of compound G (10.5 g, 20.7 mmol) in DMF (150 mL) was added $K_2CO_3$ (3.4 g, 20.7 mmol) followed by 1H-tetrazole (2.6 g, 37.1 mmol) at RT. The reaction mixture was heated to 70° C. for 16 h. Progress of the reaction was monitored by TLC. The reaction mixture was allowed to cool to room temperature and diluted with water (300 mL). The aqueous layer was extracted with ethyl acetate (3×300 mL). The organic layer was dried over anhydrous Na$_2$SO$_4$ and concentrated in vacuo. The crude compound was purified by column chromatography (SiO$_2$, 60-120 mesh) to afford 12 (6 g, 10.38 mmol, 50.4%) as a white solid. $^1$H NMR (500 MHz, CDCl$_3$): δ 8.76 (s, 1H), 8.70 (s, 1H), 7.95 (d, J=8.0 Hz, 1H), 7.70 (s, 1H), 7.64 (d, J=8.5 Hz, 1H), 7.54 (d, J=8.5 Hz, 2H), 7.42-7.37 (m, 1H), 7.08 (d, J=8.5 Hz, 2H), 6.79-6.75 (m, 1H), 6.69-6.66 (m, 1H), 5.58 (d, J=14.0 Hz, 1H), 5.14 (d, J=14.0 Hz, 1H), 4.48 (t, J=12.0 Hz, 2H). MS (ESI): m/z 578.1 [M$^+$+1].

Chiral Preparative HPLC of Enantiomers:

The enantiomers of 12 (6 g, 10.3 mmol) were separated by normal-phase preparative high performance liquid chromatography (Chiralpak IA, 250×21.2 mm, 5μ; using (A) n-hexane-(B) ethanol (A:B: 80:20) as a mobile phase; Flow rate: 12 mL/min) to obtain 12(+) (2.1 g) and 12(−) (2.0 g).

Analytical Data for 12 (+):

$^1$H NMR (500 MHz, CDCl$_3$): δ 8.76 (s, 1H), 8.70 (s, 1H), 7.95 (d, J=8.0 Hz, 1H), 7.70 (s, 1H), 7.64 (d, J=8.5 Hz, 1H), 7.54 (d, J=8.5 Hz, 2H), 7.42-7.37 (m, 1H), 7.08 (d, J=8.5 Hz, 2H), 6.79-6.75 (m, 1H), 6.69-6.66 (m, 1H), 5.58 (d, J=14.0 Hz, 1H), 5.14 (d, J=14.0 Hz, 1H), 4.48 (t, J=12.0 Hz, 2H). HPLC: 98.1%. MS (ESI): m/z 578.1 [M$^+$+1].

Chiral HPLC: $R_t$=14.12 min (Chiralpak IA, 250×4.6 mm, 5μ; mobile phase (A) n-Hexane (B) ethanol (A:B: 80:20); flow Rate: 1.00 mL/min).

Optical rotation $[\alpha]_D^{25}$: +22.3° (C=0.1% w/v in MeOH).

Example 13

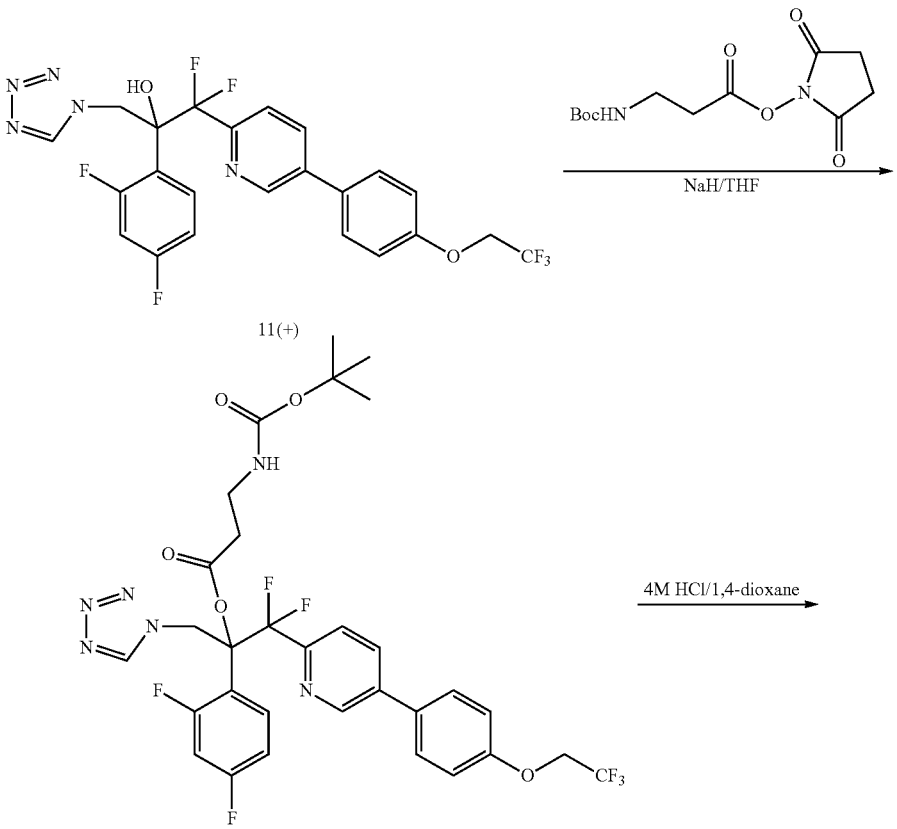

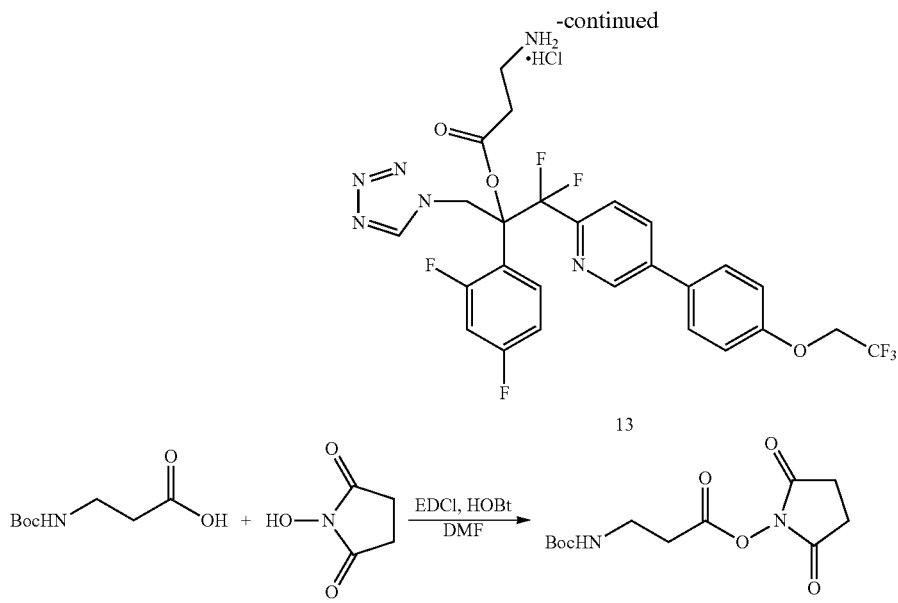

2-(2,4-difluorophenyl)-1,1-difluoro-3-(1H-tetrazol-1-yl)-1-(5-(4-(2,2,2-trifluoroethoxy)phenyl)pyridin-2-yl)propan-2-yl 3-aminopropanoate (13)

A mixture of N-Boc-β-Ala-OH (1 g, 5.29 nmol), N-hydroxysuccinimide (0.9 g, 7.82 mmol) in DMF (10 mL) were added HOBt (0.7 g, 5.25 mmol) and EDCI.HCl (1 g, 5.23 mmol) at 5° C. The reaction mixture was warmed to RT and stirred for 16 h. The progress of the reaction was monitored by TLC. The reaction was quenched with water and extracted with ethyl acetate (2×150 mL). The combined organic layers were washed with water (3×100 mL), brine (150 mL), dried over anhydrous $Na_2SO_4$ and concentrated under reduced pressure. The crude compound was triturated with ether (2×25 mL) to afford N-Boc-β-Ala-OSu (1.1 g, crude) as white solid. $^1$H NMR (500 MHz, $CDCl_3$): δ 5.10 (bs, 1H), 3.52 (q, J=6.0 Hz, 2H), 2.85-2.82 (m, 6H), 1.31 (s, 9H).

To a suspension of 11-(+) (0.2 g, 0.38 mmol) in dry THF (20 mL) was added NaH (0.02 g, 1.17 mmol) at 0° C. and stirred for 30 min at RT. N-Boc-β-Ala-OSu (0.21 g, 0.70 mmol) was added to the reaction mixture and the stirring was continued for another 16 h at RT. The progress of the reaction was monitored by TLC. The reaction mixture was quenched with ice cold water and extracted with EtOAc (2×50 mL). The combined organic layers were dried over anhydrous $Na_2SO_4$ and concentrated under reduced pressure to afford crude product, which upon separated by preparative TLC afforded compound I (38 mg, 0.06 mmol, 15%). $^1$H NMR (500 MHz, $CDCl_3$): δ 9.27 (s, 1H), 8.92 (s, 1H), 7.80 (dd, J=1.5, 8.0 Hz, 1H), 7.58 (d, J=8.5 Hz, 2H), 7.14-7.13 (m, 1H), 7.09 (d, J=8.5 Hz, 2H), 7.04 (d, J=8.0 Hz, 1H), 6.89 (t, J=7.0 Hz, 1H), 6.71-6.66 (m, 1H), 6.09 (dd, J=2.5, 15.0 Hz, 1H), 5.73 (dd, J=2.5, 15.0 Hz, 1H), 5.23 (bs, 1H), 4.45-4.40 (m, 2H), 3.46 (bs, 2H), 2.82-2.69 (m, 2H), 1.28 (s, 9H). MS (ESI): 699.3 [M$^+$+1].

To a stirred solution of compound I (0.03 g, 0.05 mmol) in 1,4-dioxane (2 mL) was added 4 M HCl solution in 1,4-dioxane (1 mL) at 5° C. and stirred for 4 h at RT. The progress of the reaction was monitored by TLC. The volatiles were evaporated under reduced pressure. The obtained crude was triturated with diethyl ether (2×25 mL) to afford 13 (0.018 g, 0.02 mmol, 55%) as a white solid. $^1$H NMR (500 MHz, DMSO-$d_6$): δ 9.67 (s, 1H), 9.04 (s, 1H), 8.13 (dd, J=1.5, 8.0 Hz, 1H), 7.88 (s, 2H), 7.78 (d, J=8.5 Hz, 2H), 7.38-7.36 (m, 1H), 7.27-7.24 (m, 1H), 7.24 (d, J=8.0 Hz, 1H), 7.17 (d, J=8.0 Hz, 1H), 6.15 (d, J=15.5 Hz, 1H), 5.54 (d, J=15.5 Hz, 1H), 4.87 (q, J=8.5 Hz, 2H), 3.06 (d, J=5.5 Hz, 2H), 2.93-2.83 (m, 2H). HPLC: 93.64%. MS (ESI): 599.4 [M$^+$+1].

Example 14

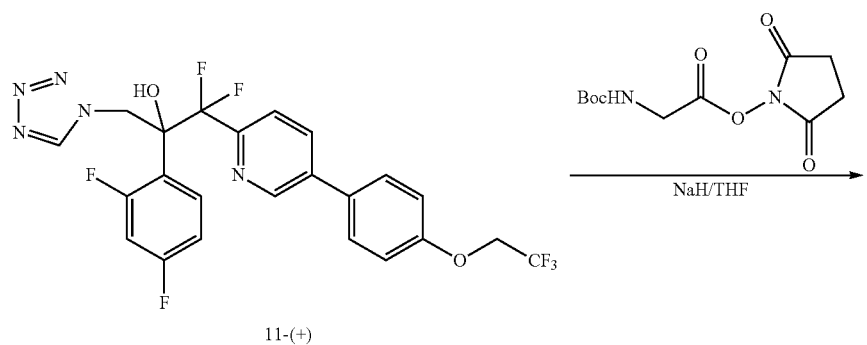

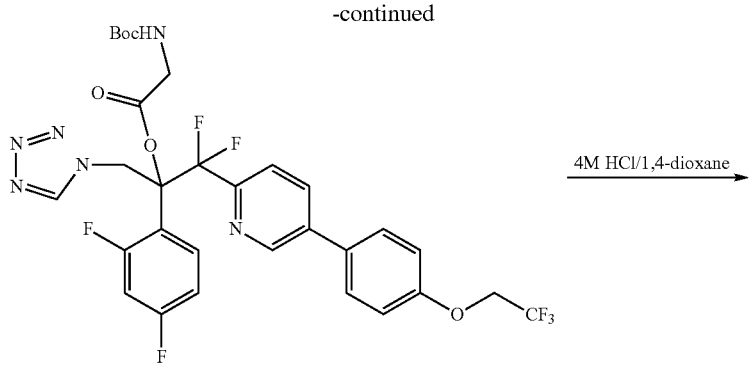

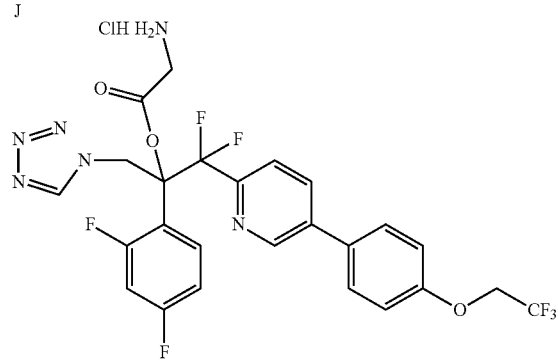

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 2-aminoacetate hydrochloride (14)

To a suspension of 11-(+) (0.1 g, 0.18 mmol) in dry THF (30 mL) was added NaH (0.01 g, 0.41 mmol) at 5° C. and stirred for 40 min at RT. N-Boc-Gly-OSu (0.1 g, 0.37 mmol) was added to the reaction mixture and the stirring was continued for another 16 h at RT. The progress of the reaction was monitored by TLC. The reaction was quenched with ice cold water and extracted with EtOAc (2×50 mL). The combined organic layers were dried over anhydrous $Na_2SO_4$ and concentrated under reduced pressure to afford crude product, which upon separated by preparative TLC afforded compound J (29 mg, 0.04 mmol, 24%). $^1$H NMR (500 MHz, DMSO-$d_6$): 9.34 (s, 1H), 8.92 (s, 1H), 7.80 (d, J=7.0 Hz, 1H), 7.59-7.54 (m, 2H), 7.44-7.42 (m, 1H), 7.10-7.03 (m, 3H), 6.94-6.91 (m, 1H), 6.64 (t, J=10.0 Hz, 1H), 6.12 (dd, J=2.5, 15.0 Hz, 1H), 5.69 (dd, J=3.5, 15.0 Hz, 1H), 5.10 (d, J=6.0 Hz, 1H), 4.43 (q, J=8.5 Hz, 2H), 4.21-4.16 (m, 1H), 3.95 (dd, J=5.0, 18.0 Hz, 1H), 1.45 (s, 9H). MS (ESI): 685.3 [M$^+$+1].

To a stirred solution of compound J (0.02 g, 0.04 mmol) in 1,4-dioxane (2 mL) was added 4 M HCl solution in 1,4-dioxane (1 mL) dropwise at 5° C. and stirred for 4 h at RT. The progress of the reaction was monitored by TLC. The volatiles were evaporated under reduced pressure. The obtained crude was triturated with diethyl ether (3×25 mL) to afford 14 (14 mg, 0.02 mmol, 60%) as a white solid. $^1$H NMR (500 MHz, DMSO-$d_6$): δ 9.68 (s, 1H), 9.04 (s, 1H), 8.45-8.43 (m, 2H), 8.14 (d, J=8.5 Hz, 2H), 7.79 (d, J=9.0 Hz, 2H), 7.45-7.44 (m, 1H), 7.29-7.27 (m, 1H), 7.24-7.23 (m, 3H), 7.14-7.10 (m, 1H), 6.18 (d, J=16.0 Hz, 1H), 5.57 (d, J=15.0 Hz, 1H), 4.87 (q, J=8.5 Hz, 2H), 4.16 (d, J=18.0 Hz, 1H), 3.94 (d, J=18.5 Hz, 1H). HPLC: 93.54%. MS (ESI): 585 [M$^+$+1].

Example 15

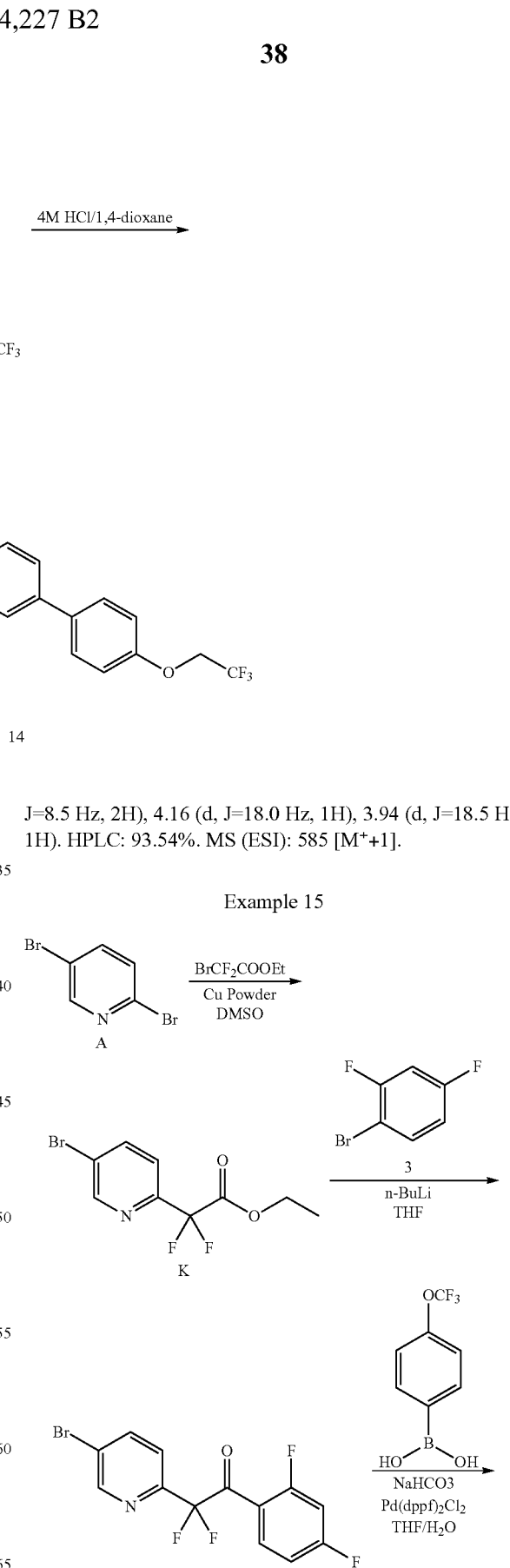

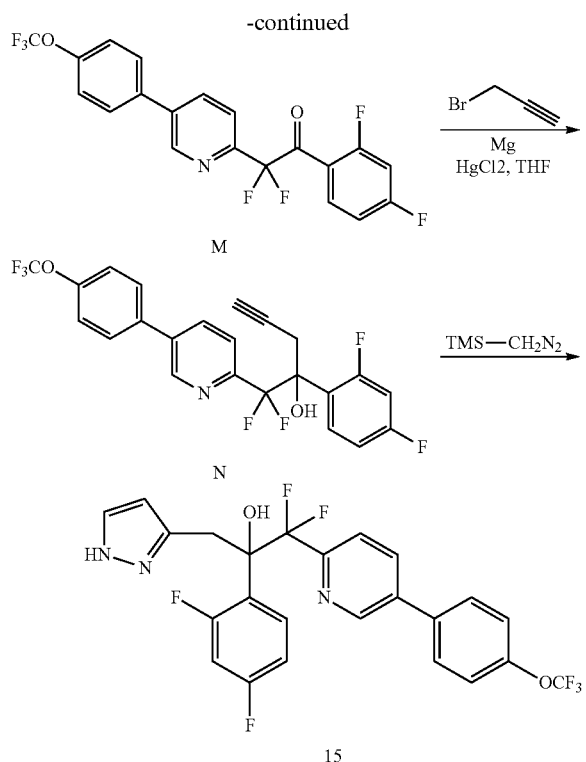

2-(2,4-Difluorophenyl)-1,1-difluoro-3-(1H-pyrazol-3-yl)-1-(5-(4-(trifluoro methoxy)phenyl)pyridin-2-yl)propan-2-ol (15)

To a suspension of copper powder (27 g, 0.42 mol) in DMSO (300 mL) was added ethyl bromo difluoro acetate (27 mL, 0.21 mol) and stirred for 1 h at RT. 2,5-Dibromopyridine (25 g, 0.10 mol) was then added and continued stirring for another 15 h at RT. The progress of the reaction was monitored by TLC. The reaction was quenched with saturated NH$_4$Cl solution (200 mL) and extracted with DCM (3×250 mL). The combined organic layers were washed with water, brine, dried over anhydrous Na$_2$SO$_4$ and concentrated under reduced pressure to afford crude product, which upon distillation under reduced pressure afforded compound K (19 g, 67.8 mmol, 64%) as a pale yellow oil. $^1$H NMR (500 MHz, CDCl$_3$): δ 8.71 (s, 1H), 8.00 (d, J=9.0 Hz, 1H), 7.62 (d, J=9.0 Hz, 1H), 4.42-4.35 (m, 2H), 1.39-1.31 (m, 3H). To a stirred solution of 2,4-difluorobromo benzene (7.6 mL, 67.8 mmol) in diethyl ether (100 mL) was added n-BuLi (42 mL, 67.85 mmol, 1.6 M in hexane) at −78° C. After being stirred for 45 min at −78° C., a solution of ester K (19 g, 67.8 mmol) in diethyl ether (100 mL) was added to the reaction mixture and the stirring was continued for another 1 h at −78° C. under inert atmosphere. The reaction mixture was warmed to room temperature at which point another 3 h stirring was given. The progress of the reaction was monitored by TLC. The reaction was quenched with saturated NH$_4$Cl solution (200 mL) and extracted with ethyl acetate (3×200 mL). The combined organic layers were washed with water, brine, dried over anhydrous Na$_2$SO$_4$ and concentrated under reduced pressure. The crude compound was purified by column chromatography (SiO$_2$, 100-200 mesh) eluting with 2% EtOAc/hexane to afford ketone L (13 g, 37.3 mmol, 55%) as yellow liquid. $^1$H NMR (500 MHz, CDCl$_3$): δ 8.62 (s, 1H), 8.08-8.04 (m, 2H), 7.72 (d, J=8.5 Hz, 1H), 7.05-6.95 (m, 1H), 6.88-6.78 (m, 1H). MS (ESI): 347[M$^+$+1], 349 [(M$^+$+2].

To a stirred solution of ketone L (1.0 g, 2.87 mmol) in THF (30 mL) and water (10 mL) were added (4-(trifluoro methoxy)phenyl boronic acid (591 mg, 2.87 mmol), NaHCO$_3$ (782 mg, 7.18 mmol) and Pd(dppf)$_2$Cl$_2$ (586 mg, 0.718 mmol) at RT under inert atmosphere. After purging with argon for a period of 30 min, the reaction mixture was heated to 65° C. and stirring was continued for 2 h. Progress of the reaction was monitored by TLC. The reaction mixture was cooled to RT and filtered through a pad of celite. The filtrate was concentrated under reduced pressure; obtained residue was dissolved in ethyl acetate (2×50 mL). The organic layer was washed with water, brine and dried over anhydrous Na$_2$SO$_4$ and concentrated under reduced pressure. The crude compound was purified by column chromatography (SiO$_2$, 100-200 mesh) to afford M (980 mg, 2.28 mmol, 79%) as light yellow sticky solid. $^1$H NMR (200 MHz, CDCl$_3$): δ 8.77 (s, 1H), 8.12-8.03 (min, 2H), 7.90 (d, J=8.4 Hz, 1H), 7.63-7.57 (m, 2H), 7.35 (d, J=8.2 Hz, 2H), 7.05-6.96 (m, 1H), 6.83-6.79 (m, 1H). Mass: m/z 430 [M$^+$+1].

To a mixture of Mg (50 mg, 2.08 mmol) and HgCl$_2$ (47 mg, 0.17 mmol) in dry THF (5 mL) was added propargyl bromide (0.05 mL, 0.34 mmol) at rt under an inert atmosphere and stirred for 20 min. The reaction mixture was then cooled to −20° C., ketone M (150 mg, 0.348 mmol) and remaining portion of propargyl bromide (0.05 mL, 0.34 mmol) in THF (5 mL) were added and continued stirring for 2 h at −20° C. The progress of the reaction was monitored by TLC. The reaction was quenched with a saturated NH$_4$Cl solution and extracted with CH$_2$Cl$_2$ (3×50 mL). The combined organic layers were washed with water, brine, dried over anhydrous Na$_2$SO$_4$ and concentrated in vacuo. The crude product was purified by column chromatography (SiO$_2$, 100-200 mesh) to afford N (110 mg, 0.23 mmol, 67%) as a solid. $^1$H NMR (200 MHz, CDCl$_3$): δ 8.86 (s, 1H), 7.96 (dd, J=8.4, 2.2 Hz, 1H), 7.65-7.57 (m, 4H), 7.41 (d, J=8.2 Hz, 2H), 6.88-6.73 (m, 2H), 6.36 (brs, 1H), 3.46 (dd, J=16.8, 2.2 Hz, 1H), 2.98 (dt, J=16.8, 2.6 Hz, 1H), 1.85 (t, J=2.6 Hz, 1H). MS (ESI): m/z 470 [M$^+$+1].

A solution of N (110 mg, 0.23 mmol) in TMSCHN$_2$ (1 mL, 1.15 mmol) was stirred at 120° C. for 15 h. The volatiles were evaporated under reduced pressure and the obtained crude material was purified by column chromatography (SiO$_2$, 100-200 mesh) to afford 15 (35 mg, 0.06 mmol, 29%) as an off white solid. $^1$H NMR (500 MHz, CDCl$_3$): δ 8.80 (s, 1H), 7.93 (d, J=8.5 Hz, 1H), 7.62-7.59 (m, 3H), 7.50-7.45 (m, 1H), 7.36-7.31 (m, 3H), 6.83 (br s, 1H), 6.70-6.65 (m, 2H), 6.04 (s, 1H), 4.02 (d, J=15.0 Hz, 1H), 3.36 (d, J=15.0 Hz, 1H). MS (ESI): m/z 512 [M$^+$+1]. HPLC: 95.6%.

Example 16

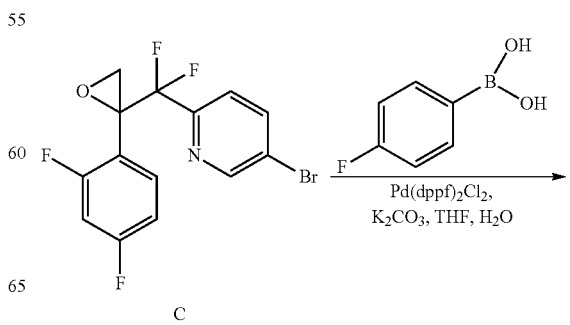

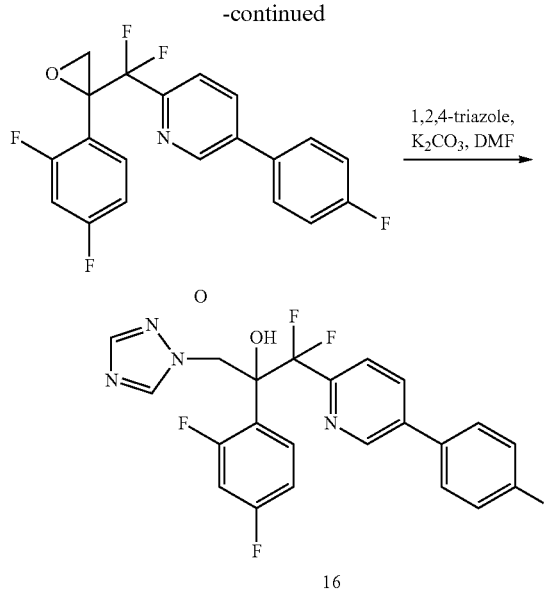

2-(2,4-Difluorophenyl)-1,1-difluoro-1-(5-(4-fluorophenyl)pyridin-2-yl)-3-(1H-1,2,4-triazol-1-yl)propan-2-ol (16)

To a stirred solution of 5-bromo-2-((2-(2,4-difluorophenyl)oxiran-2-yl)difluoromethyl)pyridine (C) (1.0 g, 2.7 mmol) in TH-F: H₂O (20 mL, 4:1 mixture) was added (4-fluorophenyl)boronic acid (378 mg, 2.7 nmol) followed by K₂CO₃ (1.1 g, 8.1 mmol) at RT and degassed by purging with inert gas for 45 min. To the resulting reaction mixture was added Pd(dppf)₂Cl₂ (197 mg, 0.27 mmol) and further degassed for 20 min at RT. The reaction mixture was then heated up to 60° C. and stirred for 4 h. After complete consumption of the starting material (by TLC), the reaction mixture was cooled to RT, diluted with water and separated the organic layer; the aqueous layer with extracted with EtOAc (2×20 mL). The combined organic extracts were dried over anhydrous Na₂SO₄ and concentrated under reduced pressure to obtain the crude. The crude material was purified by silica gel column chromatography (eluent: 20% EtOAc/hexane) to afford O (0.9 g, 2.38 mmol, 86%) as colorless semi-solid. ¹H NMR (200 MHz, CDCl₃): δ 8.85 (d, J=2.0 Hz, 1H), 7.89 (dd, J=8.2, 2.4 Hz, 1H), 7.62-7.36 (m, 4H), 7.24-7.19 (m, 2H), 6.90-6.70 (m, 2H), 3.48 (d, J=4.8 Hz, 1H), 3.02-2.98 (m, 1H).

To a stirred solution of compound O (0.3 g, 0.79 mmol) in DMF (3 mL) was added K₂CO₃ (109 mg, 0.79 mmol) followed by 1,2,4-triazole (81 mg, 1.18 mmol) at RT under inert atmosphere. The reaction mixture was then heated up to 60° C. and stirred for 16 h. After complete consumption of the starting material (by TLC), the reaction mixture was diluted with water and extracted with ethyl acetate (3×15 mL). The combined organic extracts were dried over anhydrous Na₂SO₄ and concentrated under reduced pressure to obtain the crude. The crude material was purified by silica gel column chromatography (eluent: 40% EtOAc/hexane) to afford 16 (250 mg, 0.56 mmol, 72.6%) as off-white solid. ¹H NMR (500 MHz, CDCl₃): δ 8.72 (s, 1H), 8.16 (s, 1H), 7.92 (d, J=8.5 Hz, 1H), 7.69 (s, 1H), 7.62 (d, J=8.5 Hz, 1H), 7.56-7.47 (m, 3H), 7.22-7.18 (m, 2H), 6.77-6.71 (m, 3H), 5.38 (d, J=14.0 Hz, 1H), 4.90 (d, J=14.0 Hz, 1H). MS (ESI): 447 [M⁺+1]. HPLC: 98.36%.

Example 17

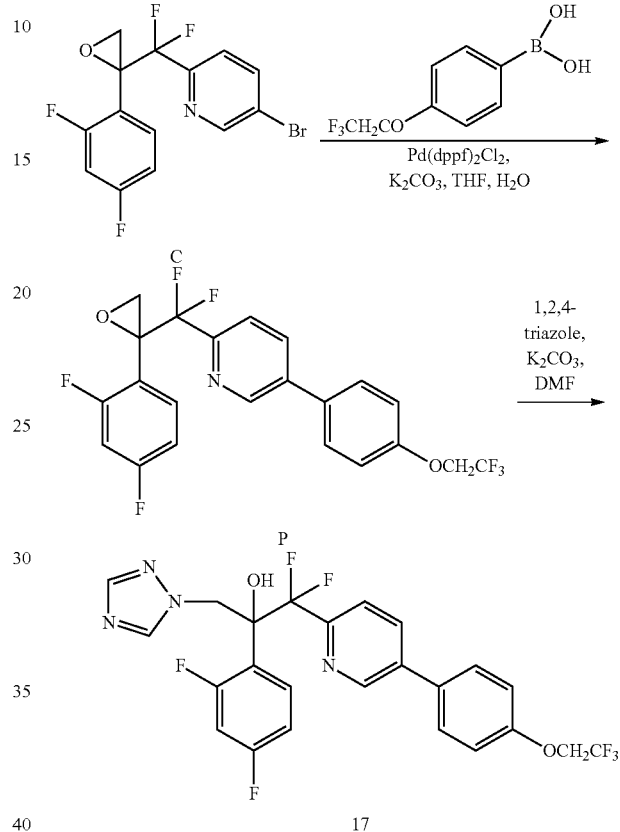

2-(2,4-difluorophenyl)-1,1-difluoro-3-(1H-1,2,4-triazol-1-yl)-1-(5-(4-(2,2,2-trifluoroethoxy)phenyl)pyridin-2-yl)propan-2-ol (17)

To a stirred solution of epoxy bromide (C) (190 mg, 0.52 mmol) in THF: H₂O (40 mL, 4:1 mixture) was added (4-(2,2,2-trifluoroethoxy)phenyl)boronic acid (174 mg, 0.57 mmol) followed by K₂CO₃ (215 mg, 1.56 mmol) at RT and degassed by purging with inert gas for 30 min. To the resulting reaction mixture was added Pd(dppf)₂Cl₂ (20 mg, 0.027 mmol) and further degassed for 20 min at RT. The reaction mixture was then heated up to 70° C. and stirred for 2 h. Progress of the reaction was monitored by TLC; the reaction mixture was cooled to RT, diluted with EtOAc (20 mL) and filtered through celite pad. The collected filtrate was washed with water (2×50 mL). The separated organic layer was dried over anhydrous Na₂SO₄ and concentrated under reduced pressure to obtain the crude. The crude material was purified by silica gel column chromatography (eluent: 15% EtOAc/hexane) to afford P (0.2 g, 0.43 mmol, 84%) as off-white solid. ¹H NMR (200 MHz, CDCl₃): δ 8.85 (d, J=2.2 Hz, 1H), 7.89 (dd, J=8.2, 2.2 Hz, 1H), 7.59-7.51 (m, 3H), 7.48-7.36 (m, 1H), 7.08 (dd, J=7.0, 2.2 Hz, 2H), 6.89-6.70 (m, 2H), 4.42 (q, J=8.2 Hz, 2H), 3.48 (d, J=5.0 Hz, 1H), 3.01-2.98 (m, 1H). MS (ESI): m/z 458 [M⁺+1].

To a stirred solution of compound P (0.2 g, 0.43 mmol) in DMF (20 mL) was added K₂CO₃ (91 mg, 0.65 mmol) followed by 1,2,4-triazole (61 mg, 0.87 mmol) at RT under inert atmosphere. The reaction mixture was then heated up to 75° C. and stirred for 7 h. After complete consumption of the starting material (by TLC), the reaction mixture was cooled to RT, diluted with water and extracted with ethyl acetate (3×75 mL). The combined organic extracts were dried over anhydrous Na₂SO₄ and concentrated under reduced pressure to obtain the crude. The crude material was purified by silica gel column chromatography (eluent: 40% EtOAc/Hexane) to afford 17 (160 mg, 0.303 mmol, 70%) as off-white solid.

Chiral Preparative HPLC of Enantiomers

The enantiomers of 17 (100 mg, 0.18 mmol) were separated by normal-phase preparative high performance liquid chromatography (Chiralpak IC, 250×19 mm, 5μ; using (A) n-hexane-(B) IPA (A:B: 60:40) as a mobile phase; Flow rate: 15 mL/min, WL 265 nm) to obtain desired (+)-17 (28 mg) (Fraction-II) and (−)-17 (28 mg) (Fraction-I).

(+)-17

¹H NMR (500 MHz, CDCl₃): δ 8.72 (s, 1H), 8.16 (s, 1H), 7.92 (dd, J=8.5, 2.0 Hz, 1H), 7.69 (s, 1H), 7.61 (d, J=8.0 Hz, 1H), 7.55 (d, J=8.0 Hz, 2H), 7.52-7.47 (m, 1H), 7.08 (d, J=9.0 Hz, 2H), 6.77-6.70 (m, 3H), 5.38 (d, J=14.5 Hz, 1H), 4.89 (d, J=14.5 Hz, 1H), 4.42 (q, J=8.0 Hz, 2H).

Optical rotation $[\alpha]_D^{24.5}$: +13.96° (C=0.1% w/v in MeOH).

Chiral HPLC: 99.9% ee (R=13.9 min) (Chiralpak IC, 250× 4.6 mm, 5μ; using n-Hexane:IPA (60:40) as a mobile phase; Flow rate: 1 mL/min, WL 265 nm).

MS (ESI): m/z 527 [M⁺+1]
HPLC: 99.86%.

Example 18

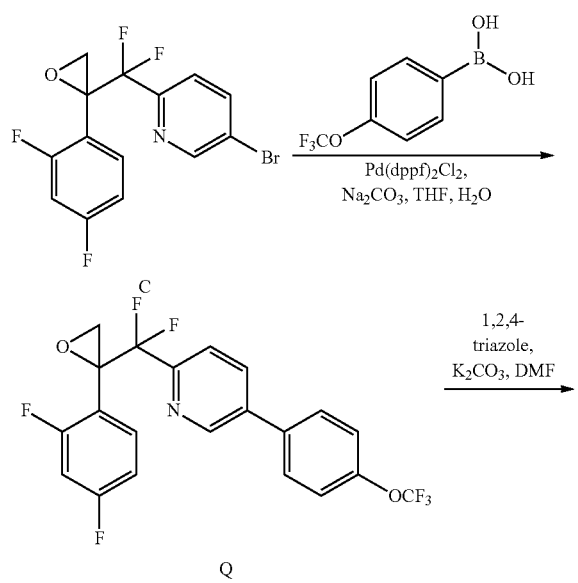

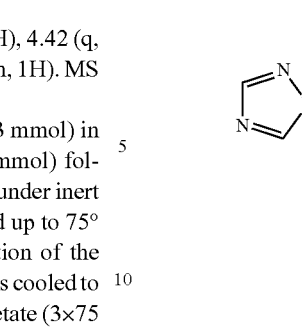

18

2-(2,4-Difluorophenyl)-1,1-difluoro-3-(1H-1,2,4-triazol-1-yl)-L-(5-(4-(trifluoromethoxy)phenyl)pyridin-2-yl)propan-2-ol (18)

To a stirred solution of epoxy bromide (C) (0.7 g, 1.93 mmol) in THF:H₂O (24 mL, 7:5 mixture) was added 4-(trifluoromethoxy)phenylboronic acid (398 mg, 1.93 mmol) followed by Pd(dppf)₂Cl₂ (394 mg, 0.48 mmol) and Na₂CO₃ (526 mg, 4.83 mmol) at RT and degassed by argon for 45 min. The resulting reaction mixture was stirred for 3 h at reflux temperature. After complete consumption of the starting material (by TLC), the reaction mixture was cooled to RT, diluted with EtOAc (20 mL) and filtered through celite bed. The collected filtrate was washed with water, brine, dried over anhydrous Na₂SO₄ and concentrated under reduced pressure to obtain the crude. The crude material was purified by silica gel column chromatography (eluent: 5% EtOAc/hexane) to afford compound Q (0.65 g, 1.46 mmol, 76%) as off-white solid.

¹H NMR (500 MHz, CDCl₃): δ 8.86 (s, 1H), 7.91 (dd, J=7.5, 2.0 Hz, 1H), 7.62 (d, J=8.5 Hz, 2H), 7.57 (d, J=7.5 Hz, 1H), 7.44-7.40 (m, 1H), 7.36 (d, J=8.5 Hz, 2H), 6.86-6.83 (m, 1H), 6.77-6.73 (m, 1H), 3.49 (d, J=5.0 Hz, 1H), 3.00 (d, J=5.5 Hz, 1H). MS (ESI): m/z 444 [M⁺+1].

To a stirred solution of compound Q (0.2 g, 0.45 mmol) in DMF (5 mL) was added K₂CO₃ (62 mg, 0.45 mmol) followed by 1,2,4-triazole (46 mg, 0.67 mmol) at RT under inert atmosphere. The reaction mixture was then heated up to 70° C. and stirred for 3 h. After consumption of the starting material (by TLC), the reaction mixture concentrated under reduced pressure, diluted with EtOAc (20 mL), washed with water and brine. The organic layer was dried over anhydrous Na₂SO₄ and concentrated under reduced pressure to obtain the crude. The crude material was purified by silica gel column chromatography (eluent: 30% EtOAc/hexane) to afford 18 (0.15 g, 0.29 mmol, 64.9%) as off-white solid. ¹H NMR (500 MHz, CDCl₃): δ 8.74 (s, 1H), 8.16 (s, 1H), 7.94 (dd, J=8.0, 2.0 Hz, 1H), 7.70 (s, 1H), 7.64 (d, J=8.5 Hz, 1H), 7.60 (d, J=8.0 Hz, 2H), 7.51-7.46 (m, 1H), 7.36 (d, J=8.5 Hz, 2H), 6.77-6.70 (m, 2H), 6.60 (s, 1H), 5.39 (d, J=14.5 Hz, 1H), 4.91 (d, J=14.5 Hz, 1H). MS (ESI): m/z 513 [M⁺+1]. HPLC: 98.86%.

Example 19

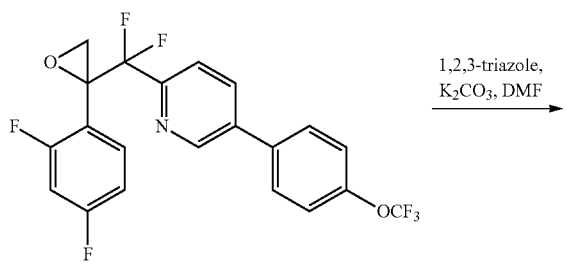

2-(2,4-Difluorophenyl)-1,1-difluoro-3-(1H-1,2,3-triazol-1-yl)-1-(5-(4-(trifluoromethoxy)phenyl)pyridin-2-yl)propan-2-ol (19)

To a stirred solution of compound Q (0.2 g, 0.45 mmol) in DMF (5 mL) was added $K_2CO_3$ (62 mg, 0.45 mmol) followed by 1,2,3-triazole (46 mg, 0.67 mmol) at RT under inert atmosphere. The reaction mixture was then heated up to 70° C. and stirred for 3 h. After consumption of the starting material (by TLC), the reaction mixture was concentrated under reduced pressure, diluted with EtOAc (20 mL), washed with water and brine. The organic layer was dried over anhydrous $Na_2SO_4$ and concentrated under reduced pressure to obtain the crude. The crude material was purified by silica gel column chromatography (eluent: 30% EtOAc/Hexane) to afford 19 (0.1 g, 0.19 mmol, 43%) as off-white solid. $^1$H NMR (500 MHz, $CDCl_3$): δ 8.71 (s, 1H), 7.95 (d, J=8.0 Hz, 1H), 7.68 (s, 1H), 7.67 (d, J=6.0 Hz, 1H) 7.59 (d, J=8.5 Hz, 2H), 7.51 (s, 1H), 7.49-7.45 (m, 1H), 7.36 (d, J=8.5 Hz, 2H), 6.77-6.69 (m, 3H), 5.55 (d, J=14.5 Hz, 1H), 5.12 (d, J=14.5 Hz, 1H). MS (ESI): m/z 513 [M$^+$+1]. HPLC: 98.99%.

Example 20

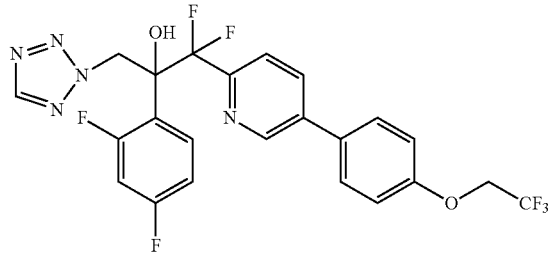 [SMILES: OC(Cn1ncnn1)(c1ccc(F)cc1F)C(F)(F)c1ccc(-c2ccc(OCC(F)(F)F)cc2)cn1]

2-(2,4-Difluorophenyl)-1,1-difluoro-3-(2H-tetrazol-1-yl)-1-(5-(4-(2,2,2-trifluoroethoxy)phenyl)pyridin-2-yl)propan-2-ol (20)

Compound 20 was prepared using the same conditions as compound 1 from P and tetrazole (0.020 g): $^1$H NMR (500 MHz, $CDCl_3$): δ 8.74 (s, 1H), 8.31 (s, 1H), 7.95 (dd, J=8.0, 2.0 Hz, 1H), 7.66 (d, J=8.0 Hz, 1H), 7.55 (d, J=9.0 Hz, 2H), 7.48-7.43 (m, 1H), 7.08 (d, J=9.0 Hz, 2H), 7.00 (s, 1H), 6.84-6.69 (m, 2H), 5.83 (d, J=14.0 Hz, 1H), 5.41 (d, J=14.0 Hz, 1H), 4.42 (q, J=8.5 Hz, 2H). MS (ESI): m/z 528 [M$^+$+1]. HPLC: 94.47%.

Example 21

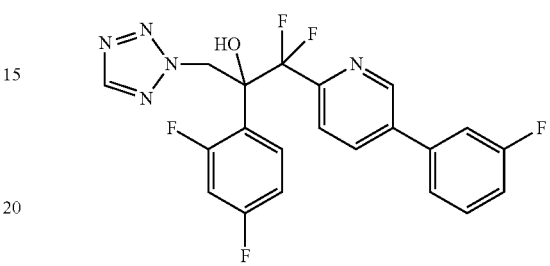

2-(2,4-Difluorophenyl)-1,1-difluoro-3-(2H-tetrazol-1-yl)-1-(5-(3-(fluorophenyl)pyridin-2-yl)propan-2-ol (21)

Compound 21 was prepared using the same conditions as compound 1 (0.017 g): $^1$H NMR (500 MHz, $CDCl_3$): δ 8.76 (s, 1H), 8.32 (s, 1H), 7.98 (d, J=8.0 Hz, 1H), 7.68 (dd, J=8.5, 4.0 Hz, 1H), 7.51-7.42 (m, 2H), 7.36 (d, J=8.0 Hz, 1H), 7.29-7.28 (m, 1H), 7.18-7.15 (m, 1), 6.84-6.79 (m, 2H), 6.73-6.69 (m, 1H), 5.84 (d, J=14.0 Hz, 1H), 5.42 (d, J=14.0 Hz, 1H). MS (ESI): m/z 448.1 [M$^+$+1]. HPLC: 98.60%.

Example 22

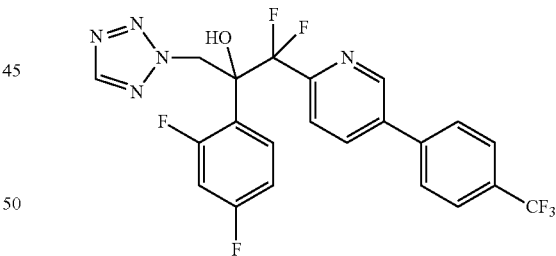

2-(2,4-Difluorophenyl)-1,1-difluoro-3-(2H-tetrazol-1-yl)-1-(5-(4-(trifluoromethylphenyl)pyridin-2-yl)propan-2-ol (22)

Compound 22 was prepared using the same conditions as compound 1 (0.020 g): $^1$H NMR (500 MHz, $CDCl_3$): δ 8.78 (s, 1H), 8.32 (s, 1H), 8.02 (dd, J=8.0, 2.0 Hz, 1H), 7.78 (d, J=8.5 Hz, 2H), 7.72-7.68 (m, 3H), 7.48-7.43 (m, 1H), 6.84-6.79 (m, 1H), 6.73-6.71 (m, 1H), 6.69 (s, 1H), 5.85 (d, J=14.0 Hz, 1H), 5.42 (d, J=14.0 Hz, 1H). MS (ESI): m/z 498.0 [M$^+$+1]. HPLC: 97.72%.

Example 23

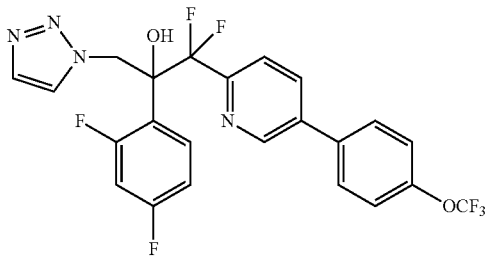 [SMILES: OC(Cn1ccnn1)(c1ccc(F)cc1F)C(F)(F)c1ccc(-c2ccc(OC(F)(F)F)cc2)cn1]

2-(2,4-Difluorophenyl)-1,1-difluoro-3-(1H-1,2,3-triazol-1-yl)-1-(5-(4-(trifluoromethylphenyl)pyridin-2-yl)propan-2-ol (23)

Compound 23 was prepared using the same conditions as compound 1 (0.037 g): $^1$H NMR (500 MHz, CDCl$_3$): δ 8.71 (s, 1H), 7.95 (d, J=8.0 Hz, 1H), 7.68-7.67 (m, 2H), 7.59 (d, J=8.5 Hz, 2H), 7.51-7.435 (m, 2H), 7.36 (d, J=8.5 Hz, 2H), 6.77-6.69 (m, 3H), 5.54 (d, J=14.5 Hz, 1H), 5.11 (d, J=14.5 Hz, 1H). MS (ESI): m/z 513.0 [M$^+$+1]. HPLC: 98.99%.

Example 24

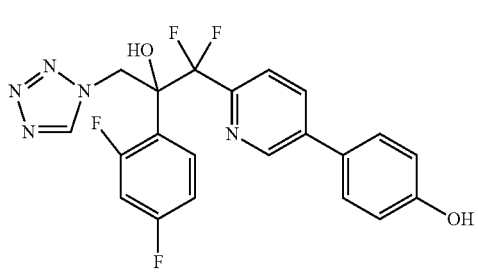 [SMILES: Oc1ccc(-c2ccc(C(F)(F)C(O)(Cn3cnnn3)c3ccc(F)cc3F)nc2)cc1]

4-(6-(2-(2,4-Difluorophenyl)-1,1-difluoro-2-hydroxy-3-(1H-tetrazol-1-yl)propyl)pyridin-3-yl)phenol (24)

Compound 24 was prepared using the same conditions as compound 1 (0.0109 g): $^1$H NMR (500 MHz, CDCl$_3$): δ 8.76 (s, 1H), 8.69 (s, 1H), 7.94 (dd, J=8.5, 2.5 Hz, 1H), 7.80 (s, 1H), 7.62 (d, J=8.0 Hz, 1H), 7.45 (d, J=8.5 Hz, 2H), 7.41-7.36 (m, 1H), 6.96 (d, J=8.5 Hz, 2H), 6.79-6.75 (m, 1H), 6.69-6.65 (m, 1H), 5.60 (d, J=14.0 Hz, 1H), 5.17 (br s, 1H), 5.13 (d, J=14.0 Hz, 1H). MS (ESI): m/z 445.9 [M$^+$+1]. HPLC: 98.55%.

Example 25

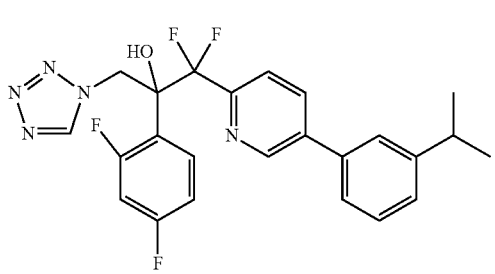 [SMILES: CC(C)c1cccc(-c2ccc(C(F)(F)C(O)(Cn3cnnn3)c3ccc(F)cc3F)nc2)c1]

2-(2,4-Difluorophenyl)-1,1-difluoro-1-(5-(3-isopropylphenyl)pyridin-2-yl)-3-(1H-tetrazol-1-yl)propan-2-ol (25)

Compound 25 was prepared using the same conditions as compound 1 (0.020 g): $^1$H NMR (500 MHz, CDCl$_3$): δ 8.76 (s, 1H), 8.75 (s, 1H), 7.99 (d, J=8.0 Hz, 1H), 7.79 (s, 1H), 7.65 (d, J=8.0 Hz, 1H), 7.45-7.33 (m, 5H), 6.79-6.75 (m, 1H), 6.68-6.65 (m, 1H), 5.62 (d, J=14.5 Hz, 1H), 5.12 (d, J=14.5 Hz, 1H), 3.02-2.96 (m, 1H), 1.30 (d, J=7.0 Hz, 6H). MS (ESI): m/z 472.1 [M$^+$+1]. HPLC: 99.50%.

Example 26

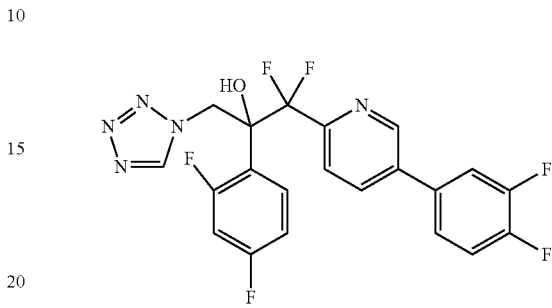

2-(2,4-Difluorophenyl)-1-(5-(3,4-difluorophenyl)pyridin-2-yl)-1,1-difluoro-3-(1H-tetrazol-1-yl)propan-2-ol (26)

Compound 26 was prepared using the same conditions as compound 1 (0.029 g): $^1$H NMR (500 MHz, CDCl$_3$): δ 8.75 (s, 1H), 8.67 (s, 1H), 7.94 (dd, J=8.0, 2.0 Hz, 1H), 7.67 (d, J=8.0 Hz, 1H), 7.58 (br s, 1H), 7.42-7.36 (m, 2H), 7.34-7.29 (m, 2H), 6.80-6.76 (m, 1H), 6.71-6.67 (m, 1H), 5.56 (d, J=14.5 Hz, 1H), 5.17 (d, J=14.5 Hz, 1H). MS (ESI): m/z 466.0 [M$^+$+1]. HPLC: 98.94%.

Example 27

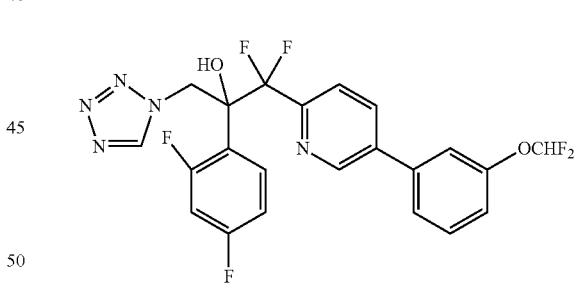

1-(5-(3-(Difluoromethoxy)phenyl)pyridin-2-yl)-2-(2,4-difluorophenyl)-1,1-difluoro-3-(1H-tetrazol-1-yl)propan-2-ol (27)

Compound 27 was prepared using the same conditions as compound 1 (0.022 g): $^1$H NMR (500 MHz, CDCl$_3$): δ 8.79 (s, 1H), 8.77 (s, 1H), 7.98 (d, J=8.0 Hz, 1H), 7.67 (d, J=8.0 Hz, 1H), 7.57 (s, 1H), 7.51 (dd, J=8.0, 2.0 Hz, 1H), 7.41-7.35 (m, 2H), 7.31 (s, 1H), 7.25-7.22 (m, 1H), 6.79-6.74 (m, 1H), 6.69-6.62 (m, 1H), 6.59 (t, J=74.0 Hz, 1H), 5.58 (d, J=14.0 Hz, 1H), 5.17 (d, J=14.0 Hz, 1H). MS (ESI): m/z 496.0 [M$^+$+1]. HPLC: 92.30%.

Example 28

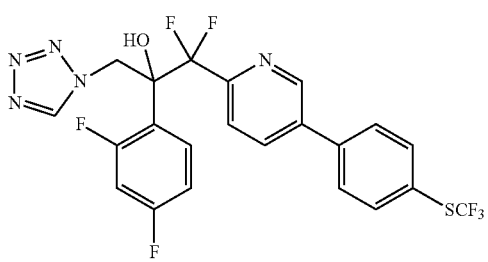

2-(2,4-Difluorophenyl)-1,1-difluoro-3-(1H-tetrazol-1-yl)-1-(5-(4-((trifluoromethyl)thio)phenyl)pyridin-2-yl)propan-2-ol (28)

Compound 28 was prepared using the same conditions as compound 1 (0.031 g): $^1$H NMR (500 MHz, CDCl$_3$): δ 8.76 (s, 1H), 8.73 (s, 1H), 8.01 (d, J=8.0 Hz, 1H), 7.80 (d, J=8.5 Hz, 2H), 7.70 (d, J=8.0 Hz, 1H), 7.61 (d, J=8.5 Hz, 2H), 7.50 (br s, 1H), 7.42-7.37 (m, 1H), 6.80-6.76 (m, 1H), 6.70-6.67 (m, 1H), 5.56 (d, J=14.5 Hz, 1H), 5.18 (d, J=14.5 Hz, 1H). MS (ESI): m/z 530.0 [M$^+$+1]. HPLC: 96.42%.

Example 29

Metalloenzyme Activity

A. Minimum Inhibitory Concentration (MIC)

Compounds were assessed for their ability to inhibit the growth of common strains of fungus, *C. albicans* using a standardized procedure (CLSI M27-A2).

Stock solutions of the test compounds and standards were prepared in DMSO at 1,600 μg/mL (*C. albicans*). Eleven, serial, one-half dilutions of compounds were prepared in 96-well plates in RPMI+MOPS. The assay concentration ranges were 6-0.016 μg/mL (*C. albicans*). Cell suspensions of *C. albicans* were prepared and added to each well at concentrations of approximately 3.7×10$^3$ colony-forming-units per milliliter (cfu/mL). All testing was in duplicate. The inoculated plates were incubated for approximately 48 h at 35±1° C. At the completion of incubation the wells of each plate were evaluated visually for the presence of fungal growth.

For fluconazole and the test compounds, the MIC was the concentration at which growth was significantly reduced (about 50% reduction). For voriconazole the MIC was the concentration which reduced *C. albicans* growth by 50% (per CLSI, M27-A2). For QC purposes *C. krusei* isolate ATCC 6258 (4.0×10$^3$ cfu/mL) was included in the VOR assay. This isolate did not exhibit trailing growth against voriconazole, therefore the MIC was the concentration at which growth was completely inhibited.

Example 30

Metalloenzyme Selectivity

A. Inhibition of Liver Cytochrome P450 Enzymes

Solutions of each test compound were separately prepared at concentrations of 20000, 6000, 2000, 600, 200, and 60 μM by serial dilution with DMSO:MeCN (50:50 v/v). The individual test compound solutions were then diluted 20-fold with DMSO:MeCN:deionized water (5:5:180 v/v/v) to concentrations of 1000, 300, 100, 30, 10, and 3 μM. Mixtures of isozyme inhibitors (sulfaphenazole, tranylcypromine, and ketoconazole as specific inhibitors of isozymes 2C9, 2C19, and 3A4, respectively) were prepared containing each inhibitor at concentrations of 6000, 2000, 600, 200, 60, 20, 6, and 2 μM by serial dilution with DMSO:ACN (50:50 v/v). The mixed inhibitor solutions were then diluted 20-fold with DMSO:MeCN:deionized water (5:5:180 v/v/v) to concentrations of 300, 100, 30, 10, 3, 1, 0.3, and 0.1 μM. The percent of organic solvent attributable to the test compound or inhibitor mixture in the final reaction mixture was 2% v/v.

Pooled human liver microsome suspension (20 mg/mL) was diluted with phosphate buffer to obtain a 5 mg/mL suspension. A solution of NADPH was prepared in phosphate buffer at a concentration of 5 mM. Separate stock solutions of each substrate were prepared in DMSO:MeCN (50:50 v/v), mixed, and diluted in phosphate buffer to obtain a single solution containing each substrate at five times its experimentally determined K$_m$ concentration. The percent of organic solvent attributable to substrate mixture in the final reaction mixture was 1% v/v.

Substrate solution and microsome suspension were combined in a 1:1 volume ratio, mixed, and distributed to reaction wells of a PCR plate. Individual test compound or combined inhibitor solutions at each concentration were added to the wells and mixed by repetitive aspirate-dispense cycles. For active controls, blank phosphate buffer solution was added in place of test compound solution. Reaction mixtures were allowed to equilibrate at 37° C. for approximately two minutes before adding NADPH solution to initiate reaction, followed by pipette mixing of reaction mixture. Ten minutes after addition of NADPH, the reaction mixtures were quenched with cold acetonitrile. The samples were mixed by orbital shaking for approximately one minute and centrifuged at 2900 RCF for ten minutes. A portion of the supernatant was analyzed by gradient reverse-phase HPLC with detection by electrospray ionization triple quadrupole mass spectrometry in the positive ion mode.

Data was fitted to sigmoid dose-response curves and the inhibitory potency of each test compound was determined as its IC$_{50}$ value.

Results

| Example | *Candida* MIC* | CYP2C9 IC50 | CYP2C19 IC50 | CYP3A4 IC50 |
| --- | --- | --- | --- | --- |
| 1 | ≤0.016 | >60 | 35 | 16 |
| 2 | ≤0.016 | >60 | >60 | >60 |
| 16 | 0.002 | 4.3 | 4.1 | 1.4 |
| 17 | ≤0.001 | 40 | 40 | 5.8 |
| 18 | ≤0.001 | 3.1 | 11 | 3.8 |
| Fluconazole | 0.5 | 29 | 8.2 | 8.0 |
| Voriconazole | 0.016 | 14 | 15 | 13 |

*Candida albicans* MIC (median inhibitory concentration) values expressed in ug/mL; CYP IC50s are in uM.

Compound examples 3-15 and 19-28 exhibit *Candida* MICs in the range of <0.016-4.0 ug/mL.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A method of inhibiting metalloenzyme activity comprising contacting a compound of formula (I), or salt thereof, with a metalloenzyme, wherein:

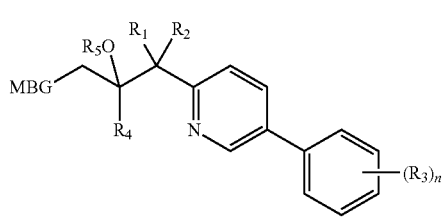

MBG is optionally substituted tetrazolyl, optionally substituted triazolyl, or optionally substituted pyrazolyl;
$R_1$ is halo;
$R_2$ is halo;
each $R_3$ is independently alkyl, cyano, haloalkyl, alkoxy, halo, haloalkoxy;
$R_4$ is aryl optionally substituted with 0, 1, 2 or 3 independent $R_3$;
$R_5$ is H, or —C(O)alkyl optionally substituted with amino;
n is 0, 1, 2 or 3; and
the metalloenzyme is lanosterol demethylase (CYP51).

2. A method of treating a subject suffering from or susceptible to a metalloenzyme-related disorder or disease, comprising administering to the subject an effective amount of a compound of formula (I), or salt, thereof, wherein:

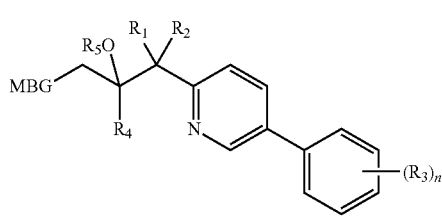

MBG is optionally substituted tetrazolyl, optionally substituted triazolyl, or optionally substituted pyrazolyl;
$R_1$ is halo;
$R_2$ is halo;
each $R_3$ is independently alkyl, cyano, haloalkyl, alkoxy, halo, haloalkoxy;
$R_4$ is aryl optionally substituted with 0, 1, 2 or 3 independent $R_3$;
$R_5$ is H, or —C(O)alkyl optionally substituted with amino;
n is 0, 1, 2 or 3; and
the metalloenzyme-related disorder or disease is mediated by lanosterol demethylase (CYP51).

3. The method of claim 1, wherein the disease or disorder is superficial fungal infection, mucosal fungal infection, systemic fungal infection, or onychomycosis.

4. A method of treating a subject suffering from or susceptible to a disorder or disease, wherein the subject has been identified as in need of treatment for the disorder or disease, comprising administering to said subject in need thereof, an effective amount of a compound of formula (I), or salt, thereof, wherein:

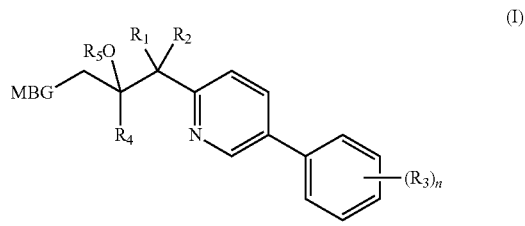

MBG is optionally substituted tetrazolyl, optionally substituted triazolyl, or optionally substituted pyrazolyl;
$R_1$ is halo;
$R_2$ is halo;
each $R_3$ is independently alkyl, cyano, haloalkyl, alkoxy, halo, haloalkoxy;
$R_4$ is aryl optionally substituted with 0, 1, 2 or 3 independent $R_3$;
$R_5$ is H, or —C(O)alkyl optionally substituted with amino;
n is 0, 1, 2 or 3;
wherein the disorder or disease is selected from one or more of the group consisting of superficial fungal infection, mucosal fungal infection, systemic fungal infection, *Aspergillosis, Blastomycosis, Candidiasis, Chromomycosis, Coccidioidomycosis, Cryptococcosis, Dermatophytosis, Histoplasmosis, Keratomycosis, Lobomycosis, Malassezia* infection, *Mucormycosis, Onychomycosis, Paracoccidioidomvcosis, Penicillium marneffei* infection, *Phaeohyphomycosis, Pneumocyctis pneumonia*, and tinea (*unguium, capitis, corporis, pedis, tonsurans, versicolor*).

5. The method of claim 4, wherein the disorder or disease is tinea (unguium).

6. The method of claim 4, wherein $R_1$ is fluoro.

7. The method of claim 4, wherein $R_2$ is fluoro.

8. The method of claim 4, wherein $R_1$ and $R_2$ are fluoro.

9. The method of claim 4, wherein $R_4$ is phenyl optionally substituted with 0, 1, 2 or 3 independent halo.

10. The method of claim 4, wherein $R_4$ is phenyl optionally substituted with 0, 1, 2 or 3 independent fluoro.

11. The method of claim 4, wherein $R_4$ is 2,4-difluorophenyl.

12. The method of claim 4, wherein $R_5$ is H.

13. The method of claim 4, wherein $R_5$ is amino substituted acyl.

14. The method of claim 4, wherein:
$R_1$ is fluoro;
$R_2$ is fluoro;
$R_4$ is 2,4-difluorophenyl; and
$R_5$ is H.

15. The method of claim 4, wherein:
each $R_3$ is independently cyano, haloalkyl, alkoxy, halo, haloalkoxy, and
n is 1 or 2.

16. The method of claim 4, wherein:
each $R_3$ is independently cyano, haloalkyl, alkoxy, halo, haloalkoxy, and
n is 1.

17. The method of claim 4, wherein the compound of formula (I) is one of:

4-(6-(2-(2,4-Difluorophenyl)-1,1-difluoro-2-hydroxy-3-(1H-tetrazol-1-yl)propyl)pyridin-3-yl)benzonitrile (1);

2-(2,4-Difluorophenyl)-1,1-difluoro-3-(1H-tetrazol-1-yl)-1-(5-(4-(trifluoromethyl)phenyl)pyridin-2-yl)propan-2-ol (2);

3-(6-(2-(2,4-Difluorophenyl)-1,1-difluoro-2-hydroxy-3-(1H-tetrazol-1-yl)propyl)pyridin-3-yl)benzonitrile (3);

2-(2,4-Difluorophenyl)-1,1-difluoro-1-(5-(4-isopropoxyphenyl)pyridin-2-yl)-3-(1H-tetrazol-1-yl)propan-2-ol (4);

2-(2,4-Difluorophenyl)-1,1-difluoro-1-(5-(4-fluorophenyl)pyridin-2-yl)-3-(1H-tetrazol-1-yl)propan-2-ol (5);

2-(2,4-Difluorophenyl)-1,1-difluoro-3-(1H-tetrazol-1-yl)-1-(5-(3-(trifluoromethoxy)phenyl)pyridin-2-yl)propan-2-ol (6);

2-(2,4-Difluorophenyl)-1,1-difluoro-3-(1H-tetrazol-1-yl)-1-(5-(4-(trifluoromethoxy)phenyl)pyridin-2-yl)propan-2-ol (7);

1-(5-(3-Chlorophenyl)pyridin-2-yl)-2-(2,4-difluorophenyl)-1,1-difluoro-3-(1H-tetrazol-1-yl)propan-2-ol (8);

1-(5-(4-Chlorophenyl)pyridin-2-yl)-2-(2,4-difluorophenyl)-1,1-difluoro-3-(1H-tetrazol-1-yl)propan-2-ol (9);

2-(2,4-Difluorophenyl)-1-(5-(2,5-difluorophenyl)pyridin-2-yl)-1,1-difluoro-3-(1H-tetrazol-1-yl)propan-2-ol (10);

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-ol (11);

2-(2,4-Difluorophenyl)-1,1-difluoro-1-(5-(4-(2,2,3,3,3-pentafluoropropoxy)phenyl)pyridin-2-yl)-3-(1H-tetrazol-1-yl)propan-2-ol (12);

2-(2,4-difluorophenyl)-1,1-difluoro-3-(1H-tetrazol-1-yl)-1-(5-(4-(2,2,2-trifluoroethoxy)phenyl)pyridin-2-yl)propan-2-yl 3-aminopropanoate (13);

2-(2,4-Difluorophenyl)-1,1-difluoro-3-(1H-tetrazol-1-yl)-1-(5-(4-(2,2,2-trifluoroethoxy)phenyl)pyridin-2-yl)propan-2-yl 2-aminoacetate hydrochloride (14);

2-(2,4-Difluorophenyl)-1,1-difluoro-3-(1H-pyrazol-3-yl)-1-(5-(4-(trifluoro methoxy)phenyl)pyridin-2-yl)propan-2-ol (15);

2-(2,4-Difluorophenyl)-1,1-difluoro-1-(5-(4-fluorophenyl)pyridin-2-yl)-3-(1H-1,2,4-triazol-1-yl)propan-2-ol (16);

2-(2,4-difluorophenyl)-1,1-difluoro-3-(1H-1,2,4-triazol-1-yl)-1-(5-(4-(2,2,2-trifluoroethoxy)phenyl)pyridin-2-yl)propan-2-ol (17);

2-(2,4-Difluorophenyl)-1,1-difluoro-3-(1H-1,2,4-triazol-1-yl)-1-(5-(4-(trifluoromethoxy)phenyl)pyridin-2-yl)propan-2-ol (18);

2-(2,4-Difluorophenyl)-1,1-difluoro-3-(1H-1,2,3-triazol-1-yl)-1-(5-(4-(trifluoromethoxy)phenyl)pyridin-2-yl)propan-2-ol (19);

2-(2,4-Difluorophenyl)-1,1-difluoro-3-(2H-tetrazol-1-yl)-1-(5-(4-(2,2,2-trifluoroethoxy)phenyl)pyridin-2-yl)propan-2-ol (20);

2-(2,4-Difluorophenyl)-1,1-difluoro-3-(2H-tetrazol-1-yl)-1-(5-(3-(fluorophenyl)pyridin-2-yl)propan-2-ol (21);

2-(2,4-Difluorophenyl)-1,1-difluoro-3-(2H-tetrazol-1-yl)-1-(5-(4-(trifluoromethylphenyl)pyridin-2-yl)propan-2-ol (22);

2-(2,4-Difluorophenyl)-1,1-difluoro-3-(1H-1,2,3-triazol-1-yl)-1-(5-(4-(trifluoromethylphenyl)pyridin-2-yl) propan-2-ol (23);

4-(6-(2-(2,4-Difluorophenyl)-1,1-difluoro-2-hydroxy-3-(1H-tetrazol-1-yl)propyl)pyridin-3-yl)phenol (24);

2-(2,4-Difluorophenyl)-1,1-difluoro-1-(5-(3-isopropylphenyl)pyridin-2-yl)-3-(1H-tetrazol-1-yl)propan-2-ol (25);

2-(2,4-Difluorophenyl)-1-(5-(3,4-difluorophenyl)pyridin-2-yl)-1,1-difluoro-3-(1H-tetrazol-1-yl)propan-2-ol (26);

1-(5-(3-(Difluoromethoxy)phenyl)pyridin-2-yl)-2-(2,4-difluorophenyl)-1,1-difluoro-3-(1H-tetrazol-1-yl)propan-2-ol (27);

2-(2,4-Difluorophenyl)-1,1-difluoro-3-(1H-tetrazol-1-yl)-1-(5-(4-((trifluoromethyl)thio)phenyl)pyridin-2-yl)propan-2-ol (28).

18. The method of claim 4, wherein the disease or disorder is superficial fungal infection, mucosal fungal infection, systemic fungal infection, or onychomycosis.

19. The method of claim 18, wherein the said superficial fungal infection comprises a skin or a nail infection.

20. The method of claim 18, wherein the said systemic fungal infection comprises an invasive fungal infection.

\* \* \* \* \*